(12) United States Patent
Kamakoti et al.

(10) Patent No.: US 11,318,451 B2
(45) Date of Patent: May 3, 2022

(54) MOLECULAR SIEVES AND A PROCESS FOR MAKING MOLECULAR SIEVES

(71) Applicant: ExxonMobil Research and Engineering Company, Annandale, NJ (US)

(72) Inventors: Preeti Kamakoti, Summit, NJ (US); Scott J. Weigel, Allentown, PA (US); Karl G. Strohmaier, Port Murray, NJ (US); Helge Jaensch, Grimbergen (BE); Marc H. Anthonis, Hofstade (BE); Martine Dictus, Willebroek (BE); Brita Engels, Aarschot (BE); Darryl D. Lacy, Easton, PA (US); Sina Sartipi, Woluwe-Saint-Lambert (BE); Brandon J. O'Neill, Lebanon, NJ (US)

(73) Assignee: ExxonMobil Research & Engineering Company, Annandale, NJ (US)

(*) Notice: Subject to any disclaimer, the term of this patent is extended or adjusted under 35 U.S.C. 154(b) by 23 days.

(21) Appl. No.: 16/545,464

(22) Filed: Aug. 20, 2019

(65) Prior Publication Data
US 2020/0061593 A1 Feb. 27, 2020

Related U.S. Application Data

(60) Provisional application No. 62/723,118, filed on Aug. 27, 2018.

(51) Int. Cl.
*B01J 29/40* (2006.01)
*B01J 29/08* (2006.01)
(Continued)

(52) U.S. Cl.
CPC ............... *B01J 29/40* (2013.01); *B01J 29/08* (2013.01); *B01J 29/703* (2013.01);
(Continued)

(58) Field of Classification Search
CPC ........ C01B 39/46; C01B 39/48; B01J 29/703; B01J 29/7038
See application file for complete search history.

(56) References Cited

U.S. PATENT DOCUMENTS

| 4,205,053 A | 5/1980 | Rollmann et al. |
| 5,063,038 A | 11/1991 | Kirker et al. |
| (Continued) | | |

FOREIGN PATENT DOCUMENTS

| CN | 103232044 A | * | 8/2013 |
| CN | 103301877 A | | 9/2013 |
| (Continued) | | | |

OTHER PUBLICATIONS

Jo et al, Capping with Multivalent Surfactants for Zeolite Nanocrystal Synthesis**, Angew. Chem. Int. Ed. 2013, 52, 10014-10017 (Year: 2013) (Year: 2013).*

(Continued)

*Primary Examiner* — Colin W. Slifka

(57) ABSTRACT

Processes are provided for preparing molecular sieves of framework structure MEI, TON, MRE, MWW, MFS, MOR, FAU, EMT, or MSE. The process involves preparing a synthesis mixture for the molecular sieve wherein the synthesis mixture includes a morphology modifier L selected from the group consisting of cationic surfactants having a quaternary ammonium group comprising at least one hydrocarbyl group having at least 12 carbon atoms, nonionic surfactants, anionic surfactants, sugars and combinations thereof.

8 Claims, 8 Drawing Sheets

(51) Int. Cl.
*B01J 29/70* (2006.01)
*B01J 29/78* (2006.01)
*B01J 35/10* (2006.01)
*B01J 37/08* (2006.01)
*C10G 3/00* (2006.01)
*C10G 35/095* (2006.01)

(52) U.S. Cl.
CPC ....... *B01J 29/7026* (2013.01); *B01J 29/7034* (2013.01); *B01J 29/7038* (2013.01); *B01J 29/7042* (2013.01); *B01J 29/7046* (2013.01); *B01J 29/7892* (2013.01); *B01J 35/1004* (2013.01); *B01J 37/08* (2013.01); *C10G 3/44* (2013.01); *C10G 35/095* (2013.01); *B01J 2229/183* (2013.01); *B01J 2229/34* (2013.01)

(56) References Cited

U.S. PATENT DOCUMENTS

| | | | |
|---|---|---|---|
| 5,182,090 | A | 1/1993 | Dwyer et al. |
| 5,232,579 | A | 8/1993 | Absil et al. |
| 5,401,896 | A | 3/1995 | Kuehl et al. |
| 5,785,947 | A | 7/1998 | Zones et al. |
| 2002/0090337 | A1 | 7/2002 | Corma Canos et al. |
| 2007/0191658 | A1 | 8/2007 | Lai |
| 2012/0202006 | A1 | 8/2012 | Rimer |
| 2016/0121315 | A1 | 5/2016 | Zhang et al. |
| 2016/0122193 | A1 | 5/2016 | Lai et al. |

FOREIGN PATENT DOCUMENTS

| | | |
|---|---|---|
| CN | 103232044 B | 4/2015 |
| CN | 105016354 A | 11/2015 |
| EP | 0026962 A1 | 4/1981 |
| EP | 0197775 A2 | 10/1986 |
| WO | 9629284 A1 | 9/1996 |

OTHER PUBLICATIONS

N Gao et al., "Development of hierarchical MCM-49 zeolite with intracrystalline mesopores and improved catalytic performance in liquid alkylation of benzene with ethylene", Microporous and Mesoporous Materials vol. 212, Aug. 2015, pp. 1-7.

Lupulescu et al., "A facile strategy to design zeolite L crystals with tunable morphology and surface architecture", J. Am. Chem. Soc. 2013, 135, 6608-6617.

Kumar et al., "SSZ-13 crystallization by particle attachment and deterministic pathways to crystal size control", J. Am Chem. Soc. 2015, 137, 13007-13017.

Blasco et al., "Changing the Si distribution in SAPO-11 by synthesis with surfactants improves the hydroisomerization/dewaxing properties", J. Catalysis, 2006, 242, 153-161.

Kim et al., "n-Heptane hydroisomerization over Pt/MFI zeolite nanosheets: Effects of zeolite crystal thickness and platinum location", J. Catalysis, 2013, 301, 187-197.

Charnell, "Gel growth of large crystals of sodium A and sodium X zeolites", J. Crystal Growth, 1971, 8, 291-294.

Chauhan et al., "Synthesis of zeolite ZSM-5: Effect of emulsifiers", Cryst. Res. Tech. 2012, 7, 746-753.

Axnanda et al., "Cationic microemulsion-mediated synthesis of silicalite-1", Microporous and Mesoporous Mater. 2005, 84, 236-246.

Lee et al., "Modifying zeolite particle morphology and size using water/oil /surfactant mixtures as confined domains for zeolite growth", Chem Commun 2004, 680-681.

Carr et al., "Non-ionic-microemulsion mediated growth of zeolite A", Microporous and Mesoporous Mater. 2005, 85, 284-292.

Kim et al., "External Surface Catalytic Sites of Surfactant-Tailored Nanomorphic Zeolites for Benzene Isopropylation to Cumene", ACS Catalysis 2013, 3, 192-195.

Chauhan et al., "Synthesis of small-sized ZSM-5 zeolites employing mixed structure directing agents", Materials Letters 2012, 74, 115-117.

Moteki et al., "From charge density mismatch to a simplified, more efficient seed-assisted synthesis of UZM-4", Chemistry of Materials 2013, 25, 2603-2609.

Mohamed et al., "Synthesis of ZSM-5 zeolite of improved bulk and surface properties via mixed templates", J. Mater. Sci. 2007, 42, 4066-4075.

Wu et al., "Mesoporous SSZ-13 zeolite prepared by a dual-template method with improved performance in the methanol-to-olefins reaction", J. Catalysis 2013, 298, 27-40.

Berger et al., "The synthesis of large crystals of zeolite Y re-visited", Microporous and Mesoporous Materials 2005, 83, 333-344.

Yu et al., "Studies on the dual-tern plating function of TBA for the formation of ZSM-11 intergrowth morphology", Ind. Eng.Chem. Res. 2015, 54, 2120-2128.

Zhu et al., "Highly mesoporous single-crystalline zeolite beta synthesized using a nonsurfactant cationic polymer as a dual-function template", J. Am. Chem. Soc. 2014, 136, 2503-2510.

Lupulescu et al., "Employing molecular modifiers to tailor the crystal morphology of zeolite catalysts", 2012 AICHe Annual Meeting Conference Proceedings, Pittsburgh, 2012. American Institute of Chemical Engineers.

* cited by examiner

MOLECULAR SIEVES AND A PROCESS FOR MAKING MOLECULAR SIEVES

CROSS-REFERENCE TO RELATED APPLICATIONS

This application claims the benefit of U.S. Provisional Application No. 62/723,118, filed on Aug. 27, 2018, the entire contents of which are incorporated herein by reference.

FIELD

This invention relates to a novel process for making crystals of a molecular sieve, to a molecular sieve made by the process, and its use as hydrocarbon conversion catalyst.

BACKGROUND

Molecular sieve materials, both natural and synthetic, have been demonstrated in the past to be useful as adsorbents and to have catalytic properties for various types of hydrocarbon conversion reactions. Certain molecular sieves are ordered, porous crystalline materials having a definite crystalline structure as determined by X-ray diffraction (XRD). Certain molecular sieves such as MCM-41 are ordered and produce specific identifiable X-ray diffraction patterns, but are not strictly crystalline. Within the molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as three-dimensional framework of $SiO_4$ and Periodic Table Group 13 element oxide (e.g., $AlO_4$). The tetrahedra are typically corner-shared through oxygen atoms with the electrovalence of the tetrahedra containing the Group 13 element (e.g., aluminum, gallium or boron) being charged balanced by the inclusion of a cation, for example a proton, an alkali metal or an alkaline earth metal cation.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, and in the online Database of Zeolite Structures http://www.iza-structure.org/databases/ which are hereby incorporated by reference. A large pore zeolite generally has a pore size of at least about 6.5 to 7 Angstroms and includes LTL, MAZ, FAU, OFF, *BEA, and MOR framework type zeolites (IUPAC Commission of Zeolite Nomenclature). Examples of large pore zeolites include mazzite, offretite, zeolite L, zeolite Y, zeolite X, omega, and beta. An intermediate pore size zeolite generally has a pore size from about 4.5 Angstroms to less than about 7 Angstroms and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Angstroms to less than about 5.0 Angstroms and includes, for example, CHA, ERI, KFI, LEV, SOD, and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

While many molecular sieves, in particular zeolites, have become established commercially as adsorbents and catalysts there remains a need for improved molecular sieves, for example, as catalysts having improved activity and/or selectivity. One aspect which has received much attention recently is the crystal size of the molecular sieve. Other things being equal, a molecular sieve having a reduced crystal size will generally have an increased external surface area which may lead to increased catalytic activity through increasing the rate of adsorption onto the surface of the molecular sieve crystals and/or by reducing the length of the diffusion pathway to the interior pores of the crystal. Reducing the crystal size of a molecular sieve catalyst may also promote reactions which occur principally on the external surface of the zeolite, for example, reactions involving larger reactant molecules which, due to their size, are slow to diffuse into the interior pores.

U.S. Pat. No. 7,482,300 describes synthesis of ZSM-48 with silica to alumina ratios of 70:1 to 110:1, along with methods for using such ZSM-48 for catalytic dewaxing. The synthesis methods are described as being suitable for forming ZSM-48 crystals having a reduced or minimized content of crystals with needle morphology.

SUMMARY

The invention provides a process of preparing crystals of a molecular sieve having a framework code selected from the group consisting of MEI, TON, MRE, MWW, MFS, MOR, FAU, EMT and MSE, the process comprising the steps of:

combining at least a source of a tetravalent element X, a morphology modifier L, and water to form a synthesis mixture;

heating said synthesis mixture under crystallization conditions for a time of about 1 hour to 100 days to form the crystals of the molecular sieve wherein the molecular sieve has a framework code selected from the group consisting of MEI, TON, MRE, MWW, MFS, MOR, FAU, EMT, and MSE; and recovering said crystals of the molecular sieve from the synthesis mixture, wherein X=Si and the morphology modifier L is selected from the group consisting of cationic surfactants having a quaternary ammonium group comprising at least one alkyl having at least 12 carbon atoms, nonionic surfactants, anionic surfactants, sugars and combinations thereof, and if a structure directing agent Q is present L is different from and is present in addition to the structure directing agent Q.

Optionally, the synthesis mixture also comprises a source of hydroxide ions. Optionally, the synthesis mixture also comprises a structure directing agent Q. Optionally, the synthesis mixture also comprises a source of a trivalent element Y. Optionally, the synthesis mixture also comprises a source of a pentavalent element Z. Optionally, the synthesis mixture also comprises a source of halide ions $W^-$. Optionally, the synthesis mixture also comprises a source of alkali metal ions $M^+$ and/or a source of alkaline earth metal cations $M^{2+}$. Optionally, the synthesis mixture also comprises one or more other components.

The inventors have found that by conducting the synthesis of the molecular sieve in the presence of the morphology modifier L it is possible to influence the crystal growth such that the crystals of molecular sieve have modified crystal sizes and/or modified acidity, as compared to the crystals of the same molecular sieve prepared in the absence of the morphology modifier L. This allows for the production of molecular sieve crystals with novel and desirable properties. The molecular sieve crystals produced by the process of the invention may be smaller than crystals of the same molecular sieve prepared by the same process but in the absence of the morphology modifier L. Without wishing to be bound by theory, the inventors believe that the presence of the morphology modifier L may either change the distribution of trivalent elements such as Al in the crystals and/or change the way in which the crystal terminates such that access to the trivalent element is enhanced. The molecular sieve crystals produced by the process of the invention may have increased surface area, especially external surface area, as compared to crystals of the same molecular sieve prepared by the same process but in the absence of the morphology modifier L. The molecular sieve crystals produced by the process of the invention may have a greater external surface acidity, as measured for example by collidine adsorption, than crystals of the same molecular sieve prepared by the same process but in the absence of the morphology modifier L. Decreased crystal size and/or increased external surface area and/or increased external acidity can lead to an increase in activity and/or an increase in selectivity of the molecular sieve when used as a component in a catalyst, for example in a hydrocarbon conversion reaction.

The process of the invention has been found to produce zeolites with crystals having increased external surface area and/or increased surface acidity as compared to the same zeolite prepared under the same conditions but in the absence of the morphology modifier L.

In another aspect, the invention provides a molecular sieve having a framework code selected from the group consisting of MEI, TON, MRE, MWW, MFS, MOR, FAU, EMT, and MSE, in which the ratio of external surface area to internal surface area is greater than 1.2 and/or in which the ratio of internal acidity, as measured by collidine absorption, to internal acidity, as measured by ammonia absorption, is greater than 1.5.

The invention also provides the molecular sieve of the invention in its as-made form. The invention further provides the molecular sieve of the invention in its calcined form.

The invention further provides a catalyst comprising the molecular sieve of the invention.

The invention further provides a hydrocarbon conversion process comprising the step of contacting a hydrocarbon feedstock with a catalyst of the invention. In one embodiment the hydrocarbon conversion process is a dewaxing process. In another embodiment the hydrocarbon conversion process is a process for the alkylation of aromatics.

DETAILED DESCRIPTION

Figure 1:
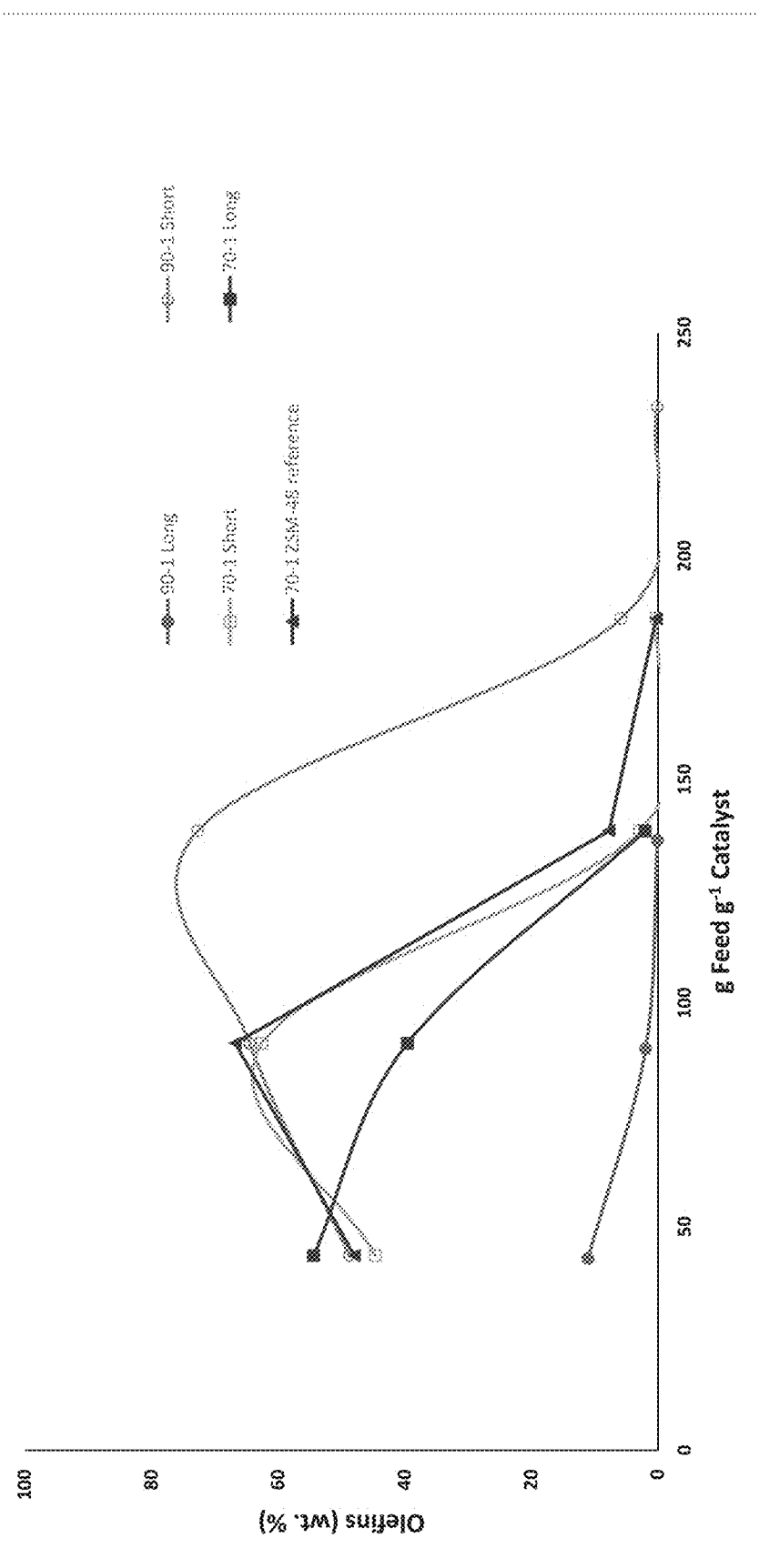
FIG. 1 shows olefin yield versus the amount of methanol exposure for various ZSM-48 catalysts.

The process of making a molecular sieve according to the invention involves preparing a synthesis mixture according to conventional techniques except that the synthesis mixture also contains a morphology modifier L. Without wishing to be bound by any theory, it is believed that the morphology modifier L may bind to or otherwise interact with the growing surfaces of crystallites within the synthesis mixture and thereby influence the morphology, including the size, aspect ratio, and agglomeration/aggregation of the final product crystals. Depending on the nature of the morphology modifier L and the concentration used the product crystals may be smaller or larger than those which would otherwise be obtained using the same synthesis mixture without the morphology modifier L under the same conditions. The morphology modifier L may also influence the distribution of any trivalent element present and so may also influence the surface acidity of the molecular sieve.

The Synthesis Mixture

As mentioned above, the synthesis mixture can be prepared according to conventional methods. The morphology modifier L may be included in the synthesis mixture at any time while crystallization is ongoing but is preferably combined with the other components before nucleation or crystallization starts. Optionally, the morphology modifier L is combined with other components of the synthesis mixture before the source of the tetravalent element X is added. For example, the water, the source of hydroxide ion (if present), the structure directing agent (if present), the source of a trivalent element Y (if present), the seeds (if present) and any other components can be combined in any order to form a mixture and then the source of the tetravalent element is combined with that mixture.

In the molecular sieves of the invention the tetravalent element X is Si. Suitable sources of silicon (Si) that can be used to prepare the synthesis mixture include silica; colloidal suspensions of silica, for Ludox®; precipitated silica; alkali metal silicates such as potassium silicate and sodium silicate; tetraalkyl orthosilicates; and fumed silicas such as Aerosil and Cabosil.

The synthesis mixture optionally also contains a source of hydroxide ions, for example, the synthesis mixture may comprise an alkali metal hydroxide such as sodium hydroxide or potassium hydroxide. Hydroxide can also be present as the anion of any charged (organic) structure directing agent or modifier which may be present or by the use of sodium aluminate or potassium aluminate as a source of Y, or by the use of sodium silicate or potassium silicate as the source of X. Sodium or potassium aluminate and silicate can also be used as the source of alkali metal $M^+$.

Optionally, the trivalent element Y is selected from the group consisting of Al, B, Fe and Ga and mixtures thereof. Optionally, Y is selected from B, Ga or Al, or mixtures thereof. Preferably, the trivalent element Y is Al. Suitable sources of trivalent element Y that can be used to prepare the synthesis mixture depend on the element Y that is selected (e.g., boron, aluminum, iron and gallium). In embodiments where Y is boron, sources of boron include boric acid, sodium tetraborate and potassium tetraborate. Optionally, the trivalent element Y is aluminum, and the aluminum source includes aluminum sulfate, aluminum nitrate, aluminum hydroxide, hydrated alumina, such as boehmite, gibbsite, and pseudoboehmite, and mixtures thereof. Other aluminum sources include, but are not limited to, other water-soluble aluminum salts, alkali metal aluminate solids or liquids, aluminum alkoxides, such as aluminum isopropoxide, or aluminum metal, such as aluminum in the form of chips or powders.

Alternatively or in addition to previously mentioned sources of Si and Al, sources containing both Si and Al elements can also be used as sources of Si and Al. Examples of suitable sources containing both Si and Al elements include amorphous silica-alumina gels or dried silica alumina powders, silica aluminas, clays, such as kaolin, metakaolin, and zeolites, in particular aluminosilicates such as synthetic faujasite and ultrastable faujasite, for instance USY, beta or other large to medium pore zeolites. Optionally, the pentavalent element Z, if present, is selected from the group consisting of P and As, and mixtures thereof. Preferably, Z, if present, is P. Suitable sources of phosphorus include one or more sources selected from the group consisting of phosphoric acid; organic phosphates, such as triethyl phosphate, tetraethyl-ammonium phosphate; aluminophosphates; phosphate salts such as alkali metal phosphates, dihydrogen phosphates, hydrogen phosphates and pyrophosphates, and mixtures thereof.

Optionally, the halide ion $W^-$, if present, is selected from the group consisting of chloride, bromide, fluoride and mixtures thereof. The source of halide ions may be any compound capable of releasing halide ions in the molecular sieve synthesis mixture. Non-limiting examples of sources of halide ions include salts containing one or several halide ions, such as metal halides, preferably where the metal is sodium, potassium, calcium, magnesium, strontium or barium. Suitable sources of fluoride ion, $F-$, include HF; ammonium fluoride or tetraalkylammonium fluorides such as tetramethylammonium fluoride or tetraethylammonium fluoride; fluoride-containing salts such as NaF, and KF; compounds of fluoride with the elements X, Y such as $AlF_3$ and $SiF_6$ salts; and/or compounds in which the fluoride ion is present as counterion for a cationic structure directing agent, Q. If the synthesis mixture does not comprise a source of hydroxide ion, then it preferably contains a source of fluoride ion, which can also act as a mineralizing agent. A convenient source of halide ion is HF.

Optionally, the synthesis mixture also contains a source of alkali metal cations $M^+$ and/or alkaline earth metal cations $M^{2+}$. If present, the alkali metal cation $M^+$ is preferably selected from the group consisting of $Li^+$, $Na^+$, $K^+$, $Rb^+$ and $Cs^+$ and mixtures thereof. Suitable sources of Na include may be a sodium salts such as NaCl, NaBr, NaF, or $NaNO_3$; sodium hydroxide, sodium aluminate and mixtures thereof. Suitable sources of $K^+$ include potassium hydroxide, potassium halides such as KCl, KF or NaBr, potassium nitrate and mixtures thereof. If present, the alkaline earth metal cation is preferably selected from $Mg^{2+}$, $Ca^{2+}$, $Sr^{2+}$, $Ba^{2+}$ and mixtures thereof.

Structure directing agents, Q, are compounds which are known to influence the crystallization of the framework of the molecular sieve so as to promote the formation of a particular desired molecular sieve. For example, tetrapropylammonium hydroxide or bromide is often used to make ZSM-5. In contrast, the role of the morphology modifier, L, is to influence the crystallization to modify the crystal size, the external surface area and/or the external acidity of the molecular sieve as described above, rather than the to influence the identity of the molecular sieve. Where the molecular sieve is one which requires the use of a structure directing agent Q the synthesis mixture will also comprise an effective concentration of the structure directing agent. In that case, the morphology modifier L will be different from and will be present in addition to the structure directing agent Q. ZSM-18, ZSM-22, ZSM-48, MCM-49, ZSM-57, mordenite, and MCM-68 require the use of a structure directing agent. The nature of the structure directing agent Q will depend upon the desired framework type. Suitable structure directing agents are known to the skilled person. The structure directing agent Q may be present in any suitable form, for example as a salt of a halide such as a chloride or bromide, as a hydroxide or as a nitrate. The structure directing agent Q will generally be an organic structure directing agent, for example, an amine such a propylamine, pyrrolidine or pyridine or a nitrogen-containing cation such as a quarternary ammonium cation. Optionally, the ammonium cation does not include any alkyl chain having more than 10 carbon atoms. For example, the structure directing agent Q may optionally be N,N,N-trimethyl-1-adamantammonium hydroxide (TMAdA) where it is desired to produce a zeolite of framework type CHA. Further structure directing agents Q and the relevant zeolites are mentioned below:

ZSM-48: hexamethonium dichloride (diquat-6-Cl2), hexamethonium dihydroxide (diquat-6-OH2), pentamethonium dichloride (diquat-5-Cl2), pentamethonium dihydroxide (diquat-5-OH2), octylamine, 1,6-diaminohexane, pyrrolidine, propylamine/tetramethylammonium hydroxide, bis(N-methylpyridyl)ethylinium, diethylenetriamine, triethylenetetraamine, tetraethylenepentaamine, 1,4,8,11-tetra-aza-undecane, 1,5,9,13-tetra-aza-undecane, 1,5,8,12-tetra-aza-undecane, 1,3-diaminopropane, trimethylamine;

ZSM-18: 2,3,4,5,6,7,8,9-octahydro-2,2,5,5,8,8-hexamethyl-1 1H-benzo[1,2-c:3,4-c':5,6-c"]tripyrrolium hydroxide and chloride, butamethonium hydroxide/tetramethylammonium hydroxide;

ZSM-22: 1-aminobutane, diethylamine, ethylene diamine, 1,3-diaminopropane, 1,6-diaminohexane, 1,4,8,11-tetra-aza-undecane, 1,5,9,13-tetra-aza-undecane, 1,5,8,12-tetra-aza-undecane, N-ethylpyridinium;

ZSM-57: hexaethyl-diquat-5 dichloride, hexaethyl-diquat-5 dihydroxide; Mordenite: tetraethylammonium hydroxide, tetraethylammonium bromide, benzyltrimethylammonium chloride, benzyltrimethylammonium hydroxide, N-ethylpyridinium bromide, N-ethylpyridinium hydroxide, trioctylamine, alkyl phenol/alkyl sulfonates;

MWW (includes MCM-49, MCM-22, MCM-56): hexamethyleneimine, aniline, piperidine, diethyldimethylammonium hydroxide, ethyltrimethylammonium hydroxide, choline chloride, choline hydroxide, N—N,N',N'-tetramethyl-1, 6-diaminohexane, triethylamine, hexamethonium dihydroxide, triethanolamine;

Hexagonal faujaite (EMT): methyltriethylammonium hydroxide, tetraethylammonium hydroxide, 18-crown-6;
Cubic faujasite (FAU): 15-crown-5;
MCM-68: N,N,N',N'-tetraethyl bicyclo[2.2.2]-oct-7-ene-2R,3S:5R,6S-dipyrrolidium diiodide, N,N,N',N'-tetraethyl bicyclo[2.2.2]-oct-7-ene-2R,3S:5R,6S-dipyrrolidium dihydroxide, N,N-dimethyl-4-cyclohexylpiperazinium hydroxide, 1-butyl-1-methylpiperidinium hydroxide.

Where those structure directing agents Q are present in a synthesis mixture to promote the formation of the relevant molecular sieve, they are not considered to be morphology modifiers L according to the present invention.

For aspects related to synthesis of ZSM-48 (or other MRE framework zeolites as described in the zeolite database maintained by the International Zeolite Association), any convenient structure directing agent suitable for use in a synthesis mixture for formation of ZSM-48 can be used as a dominant structure directing agent. One option can be to use a diquaternary alkylammonium salt with a 6 carbon atom chain between the ammonium ions (diquat-6). Another option can be to use a diquaternary alkylammonium salt with a 5 carbon atom chain between the ammonium ions (diquat-5). Both diquat-5 and diquat-6 are known to be suitable as structure directing agents for formation of ZSM-48, although the resulting ZSM-48 crystals generated by diquat-5 and diquat-6 are typically different.

The synthesis mixture can have any composition which is suitable for preparing the desired zeolite framework. The following ranges are given as examples of desirable and preferred ranges for each pair of components in the synthesis mixture. Conveniently, the molar ratio of $XO_2:Y_2O_3$ in the synthesis mixture may be in the range of from 2 to infinity (i.e. no Y), in particular from 5 to 500, preferably from 5 to 200. Optionally, in the synthesis mixture the molar ratio of structure directing agent $Q:(XO_2+Y_2O_3+Z_2O_5)$ is in the range of from 0.01 to 1.0, preferably from 0.02 to 0.9, optionally from 0.04 to 0.5. Optionally, in the synthesis mixture the molar ratio of $H_2O:(XO_2+Y_2O_3+Z_2O_5)$ is in the range of from 5 to 100. Optionally, in the synthesis mixture the molar ratio of $M^+:(XO_2+Y_2O_3+Z_2O_5)$ is in the range of from 0 to 1.2, preferably from 0 to 1.0. Optionally, in the synthesis mixture the molar ratio of $OH^-:(XO_2+Y_2O_3+Z_2O_5)$ is in the range of from 0.05 to 1.1, preferably from 0.10 to 1.0. Optionally, in the synthesis mixture the molar ratio of $halide^-:(XO_2+Y_2O_3+Z_2O_5)$ is in the range of from 0 to 1, preferably from 0 to 0.5. The reaction mixture may for example have a composition, expressed in terms of mole ratios, as indicated in the following Table 1:

TABLE 1

Synthesis Mixture Composition Ratios.

| Mole ratio | Useful | Preferred |
|---|---|---|
| $XO_2/Y_2O_3$ | 5 to 500 | 5 to 200 |
| $Q/(XO_2 + Y_2O_3 + Z_2O_5)$ | 0.00 to 1.0 | 0.02 to 0.9 |
| $H_2O/(XO_2 + Y_2O_3 + Z_2O_5)$ | 5 to 100 | 5 to 100 |
| $M^+/(XO_2 + Y_2O_3 + Z_2O_5)$ | 0 to 1.20 | 0 to 1.00 |
| $OH^-/(XO_2 + Y_2O_3 + Z_2O_5)$ | 0.05 to 1.1 | 0.10 to 1.0 |
| $Halide^-/(XO_2 + Y_2O_3 + Z_2O_5)$ | 0 to 1 | 0 to 0.5 |

The water may be added in any amount suitable to dissolve the components and to prepare the desired molecular sieve. The synthesis mixture will comprise an aqueous liquid phase and may also comprise some undissolved solid components as well as crystallised molecular sieve. The liquid present in the synthesis mixture is substantially a single phase, typically an aqueous solution, gel phase, slurry, paste or moist powder. The liquid present in the synthesis mixture typically comprises less than 5 wt %, optionally less than 2 wt %, optionally less than 1 wt % of water-insoluble liquid components. In particular, the liquid present in the synthesis mixture is not an emulsion or a microemulsion. The synthesis may be performed with or without added nucleating seeds. If nucleating seeds are added to the synthesis mixture, the seeds are suitably present in an amount from about 0.01 to 10.0% by weight, based on the synthesis mixture, such as from about 0.01 to 2.0% by weight of the synthesis mixture. The seeds can for instance be of any suitable zeolite, which may be a zeolite having the same or a different framework as the zeolite to be obtained.

The Morphology Modifier L

The morphology modifier L is selected from the group consisting of cationic surfactants having a quaternary ammonium group comprising at least one hydrocarbyl, preferably alkyl, group having at least 12 carbons atoms, nonionic surfactants, anionic surfactants, sugars and combinations thereof. The morphology modifier may be added to the synthesis mixture at any time before crystallization s completed. Optionally, the morphology modifier L is added to the other components of the synthesis mixture before nucleation or crystallization of the crystals begins. Mixtures of two or more morphology modifiers L may also be used and such processes are within the scope of the invention.

The morphology modifier may be a sugar. The sugar may be a monosaccharide or a disaccharide. Suitable monosaccharides include glucose, fructose and galactose, especially fructose. Suitable disaccharides include sucrose, maltose and lactose. The sugar may be a pentose. Alternatively, the sugar may be a hexose.

The morphology modifier L may be a cationic surfactant having a quaternary ammonium group comprising at least one hydrocarbyl having at least 12 carbon atoms. The at least one hydrocarbyl having at least 12 carbon atoms is covalently bound to the nitrogen atom of the quaternary ammonium, and may be branched or linear, preferably linear. The at least one hydrocarbyl optionally has at least 14 carbons atoms, optionally at least 16 carbon atoms, optionally at least 18 carbon atoms. Optionally, the at least one hydrocarbyl has no more than 30 carbon atoms. The alkyl may be saturated or unsaturated, preferably saturated. The cationic surfactant may comprise two hydrocarbyls each having at least 12 carbon atoms bound to the nitrogen atom of the quaternary ammonium group. The other substituents on the nitrogen atom of the quaternary ammonium group are optionally alkyl having from 1 to 8 carbon atoms, optionally from 1 to 4 carbon atoms, such as methyl groups. Each hydrocarbyl may include one or more heteroatoms, optionally selected from selected from oxygen, sulphur, nitrogen and halide.

The morphology modifier L may be a cationic surfactant having a single quaternary ammonium group comprising at least one alkyl having at least 12 carbon atoms. The at least one alkyl having at least 12 carbon atoms is covalently bound to the nitrogen atom of the quaternary ammonium, and may be branched or linear, preferably linear. The at least one alkyl optionally has at least 14 carbons atoms, optionally at least 16 carbon atoms, optionally at least 18 carbon atoms. Optionally, the at least one alkyl has no more than 30 carbon atoms. The alkyl may be saturated or unsaturated, preferably saturated. The cationic surfactant may comprise two alkyls each having at least 12 carbon atoms bound to the nitrogen atom of the quaternary ammonium group. The other substituents on the nitrogen atom of the quaternary ammonium group are optionally alkyl having from 1 to 8 carbon atoms, optionally from 1 to 4 carbon atoms, such as methyl groups.

The cationic surfactant may comprise two or more such quaternary ammonium groups. Alternatively, the cationic surfactant may comprise only a single (that is, no more than one) quaternary ammonium group.

The cationic surfactant may include any suitable anion, such as hydroxide or halide as counterion. OH$^-$, F$^-$, Cl$^-$ and Br$^-$ are preferred counterions.

The morphology modifier L is optionally a cationic surfactant having the formula (1)

$$(R^1)_q(R^2)_{4-q}N^+(X^{n-})_{1/n} \quad (1)$$

wherein each $R^1$ is independently a $C_1$-$C_6$, optionally a $C_1$ to $C_4$, hydrocarbyl group which may be linear or branched, saturated or unsaturated, preferably linear and saturated and each hydrocarbyl may include one or more heteroatoms, optionally selected from selected from oxygen, sulphur, nitrogen and halide; $R^2$ is a $C_{12}$ to $C_{30}$, optionally $C_{14}$ to $C_{30}$, optionally $C_{16}$ to $C_{30}$, optionally $C_{18}$ to $C_{30}$ hydrocarbyl which may be branched or linear, saturated or unsaturated, preferably linear and saturated, and each hydrocarbyl may include one or more aromatic or aliphatic cyclic groups, and/or one or more heteroatoms, optionally selected from selected from oxygen, sulphur, nitrogen and halide; q is 1 or 2, preferably 1; $X^{n-}$ is an anion of valency n. n is preferably 1. $X^{n-}$ is optionally a hydroxide anion or a halide anion, especially a halide anion selected from fluoride, chloride or bromide. $R^1$ is optionally methyl.

Preferably each $R^1$ is independently a $C_1$-$C_6$, optionally a $C_1$ to $C_4$, alkyl group which may be linear or branched, saturated or unsaturated, preferably linear and saturated. Preferably $R^2$ is a $C_{12}$ to $C_{30}$, optionally $C_{14}$ to $C_{30}$, optionally $C_{16}$ to $C_{30}$, optionally $C_{18}$ to $C_{30}$ alkyl group which may be branched or linear, saturated or unsaturated, preferably linear and saturated.

Optionally, the morphology modifier L is a cationic surfactant having the formula (2)

$$(R^3)_3R^4N^+A^- \quad (2)$$

in which $A^-$ is an anion, preferably hydroxide or halide, and is preferably selected from OH$^-$, Cl$^-$ and Br$^-$, each $R^3$ is independently selected from hydrogen and $C_1$ to $C_4$ alkyl, preferably methyl, and $R^4$ is a $C_{12}$ to $C_{30}$ alkyl group, preferably a $C_{14}$ to $C_{20}$ alkyl group, which may be branched or linear, and be saturated or unsaturated, and optionally contains one or more cyclic groups, and is preferably saturated and linear.

Suitable cationic surfactants include dodecyltrimethylammonium chloride, dodecyltrimethylammonium bromide, hexadecyltrimethylammonium chloride, hexadecyltrimethylammonium bromide, octadecyltrimethylammonium chloride, octadecyltrimethylammonium bromide, hexadecylethyldimethylammonium chloride, and hexadecylethyldimethylammonium bromide.

The morphology modifier L may be a nonionic surfactant. Optionally, the nonionic surfactant is selected from the group consisting of alkyl ethoxylates, alkyl propoxylates, alkylphenol ethoxylates, alkylphenol propoxylates, fatty acid ethoxylates, fatty acid propoxylates, ethoxylated amines, propoxylated amines, ethoxylated amides, propoxylated amides, block copolymers of ethylene oxide and propylene oxide, block copolymers of ethylene oxide and butylene oxide, and fatty acid esters of polyhydroxy compounds such as glycerol and sorbitan. For example, the morphology modifier L may be PEG-dodecyl ether or PEG oleyl ether. The morphology modifier L may be an anionic surfactant.

Anionic surfactants comprise an anionic group such as a sulfate, sulfonate, phosphate or carboxylate group, and an alkyl group having at least 8 carbon atoms, optionally at least 10 carbon atoms, optionally at least 12 carbon atoms for example from 14 to 30 carbon atoms, Optionally, the anionic surfactant is an alkyl sulphate, an alkyl sulfonate, an alkyl phosphate or an alkyl carboxylate. Optionally, the anionic surfactant is an alkyl sulfate such as sodium lauryl sulfate.

The molar ratio L:X in the synthesis mixture is optionally in the range of from 0.0001 to 0.10, optionally from 0.0001 to 0.08, optionally from 0.0001 to 0.05, optionally from 0.0001 to 0.03, optionally from 0.001 to 0.025. At lower ratios the concentration of morphology modifier L may be insufficient to cause noticeable change in the morphology of the crystals whereas at higher ratios the concentration of the morphology modifier may be so large as to either inhibit the crystallization so as to significantly reduce the rate of crystallization or to cause another molecular sieve framework to be formed in place of the desired one.

The morphology modifier L is optionally present in the synthesis mixture in a concentration in the range of from 0.01 wt % to 10 wt %, optionally from 0.1 wt % to 5 wt %, optionally from 0.2 wt % to 3 wt %, preferably from 0.5 wt % to 2 wt % based on the weight of the synthesis mixture.

The Crystallization and Recovery

Crystallization can be carried out under either static or stirred conditions in a suitable reactor vessel, such as for example, polypropylene jars or Teflon® bottles, acid digestion vessels, Teflon® lined or stainless steel autoclaves, plough shear mixers, or reaction kettles. The crystallization is typically carried out at a temperature of about 80° C. to about 250° C., optionally 100° C. to about 200° C., optionally about 150° C. to about 170° C., for a time sufficient for crystallization to occur at the temperature used, e.g., from about 1 day to about 100 days, in particular from 1 to 50 days, for example from about 2 days to about 40 days. Thereafter, the synthesized crystals are separated from the mother liquor by any convenient method such as filtration or centrifugation and recovered. Crystals are then dried, for example, under atmospheric conditions, washed with low boiling solvents such as acetone, methanol, ethanol, or propanol, microwave conditions, or dried in an oven at temperatures of up to 150° C.

Calcination

The process optionally includes the step of calcining the crystals recovered in step c) to give the calcined form of the molecular sieve. The conditions of calcination will be chosen to at least partially eliminate any organic residues remaining, such as remaining morphology modifier L and/or any structure directing agent Q (if used) which is typically trapped in the pores of the molecular sieve in its "as-made" form.

The calcining step typically involves heating the zeolite at a temperature of at least about 200° C., preferably at least about 300° C., more preferably at least about 370° C. for at least 1 minute and generally not longer than 20 hours. While subatmospheric pressure can be employed for the thermal treatment, atmospheric pressure is usually desired for reasons of convenience. The thermal treatment can be performed at a temperature up to about 925° C. For instance, the thermal treatment can be conducted at a temperature of from 400 to 600° C., for instance from 500 to 550° C., in the presence of an oxygen-containing gas, for example, in air.

The molecular sieve may also be subjected to an ion-exchange treatment, for example, with aqueous ammonium salts, such as ammonium nitrates, ammonium chlorides, and ammonium acetates, in order to remove remaining alkali metal cations and/or alkaline earth metal cations and to replace them with protons thereby producing the acid form of the molecular sieve. To the extent desired, the original cations of the as-synthesized material, such as alkali metal cations, can be replaced by ion exchange with other cations. Preferred replacing cations can include metal ions, hydrogen ions, hydrogen precursor, e.g., ammonium ions and mixtures thereof. Particularly preferred cations can be those which tailor the catalytic activity for certain hydrocarbon conversion reactions. These can include hydrogen, rare earth metals and metals of Groups IIA, IIIA, IVA, VA, IB, IIB, IIIB, IVB, VB, VIB, VIIB and VIII of the Periodic Table of the Elements. The ion exchange step may take place after the as made molecular sieve is dried. The ion-exchange step may take place either before or after a calcination step.

The molecular sieve may also be subjected to other treatments such as steaming and/or washing with solvent. Such treatments are well-known to the skilled person and are carried out in order to modify the properties of the molecular sieve as desired.

The Molecular Sieve

The molecular sieve of the invention and as made by the process of the invention has a framework structure code selected from the group consisting of MEI, TON, MRE, MWW, MFS, MOR, FAU, EMT and MSE. Optionally, the molecular sieve is a zeolite selected from the group consisting of ZSM-18, ZSM-22, ZSM-48, MCM-49, ZSM-57, mordenite, cubic faujasite, hexagonal faujasite and MCM-68. Details of the framework types and pore dimensionality are given in Table 2 below.

TABLE 2

Molecular Sieve Framework Types and Pore Dimensionalities.

| Molecular Sieve | Framework Type | Dimension |
| --- | --- | --- |
| ZSM-18 | MEI | 1 |
| ZSM-22 | TON | 1 |
| ZSM-48 | MRE | 1 |
| MCM-49 | MWW | 2 |
| ZSM-57 | MFS | 2 |
| Mordenite | MOR | 2 |
| Cubic Faujasite | FAU | 3 |
| Hexagonal Faujasite | EMT | 3 |
| MCM-68 | MSE | 3 |

Optionally, the molecular sieve is selected from the group consisting of ZSM-18, ZSM-22, ZSM-48, MCM-49, ZSM-57, cubic faujasite and hexagonal faujasite. Optionally, the molecular sieve is selected from the group consisting of ZSM-18 and ZSM-48. Optionally, the molecular sieve is selected from the group consisting of MCM-49, ZSM-57 and mordenite. Optionally, the molecular sieve is selected from the group consisting of cubic faujasite, hexagonal faujasite and MCM-68. ZSM-48 and MCM-49 are particularly preferred molecular sieves.

ZSM-12, ZSM-23, ZSM-50, zeolite beta, ZSM-10, chabazite and zeolite A are all further molecular sieves which may be made according to the process of the present invention and therefore the molecular sieve of the invention may in an alternate embodiment be selected from the group consisting of ZSM-12, ZSM-18, ZSM-22, ZSM-48, MCM-49, ZSM-57, cubic faujasite, hexagonal faujasite, ZSM-23, ZSM-50, zeolite beta, ZSM-10, chabazite and zeolite A.

The molecular sieve made by the process of the invention may have an increased external surface area as compared to the same molecular sieve made in the absence of the morphology modifier L. Optionally, the molecular sieve made by the process of the invention has an external surface area of at least 1.1 times, optionally at least 1.2 times the external surface area of the same molecular sieve made in the absence of the morphology modifier L.

The molecular sieve made by the process of the invention may have an increased external acidity, as measured by collidine absorption, as compared to the same molecular sieve made in the absence of the morphology modifier L. Optionally, the molecular sieve made by the process of the invention has an external acidity of at least 1.1 times, optionally at least 1.2, times the external acidity of the same molecular sieve made in the absence of the morphology modifier L.

Alternatively, the molecular sieve made by the process of the present invention has a reduced external surface area and/or a reduced external acidity as compared to the same molecular sieve made in the absence of the morphology modifier L.

By selecting the appropriate morphology modifier L and an appropriate concentration of that morphology modifier the skilled person can prepare molecular sieves having a range of external surface area, external acidity and/or crystal size.

In some aspects, for molecular sieves having a 1-dimensional pore channel structure, such as MRE (ZSM-48), small crystal size can also be beneficial for improving the lifetime of the catalyst. Without being bound by any particular theory, it is believed that for 1-dimensional pore channel molecular sieves, having a shorter crystal length in the direction of the pore channel can reduce or minimize the rate of coke formation. This can allow a larger amount of a feedstock to be processed, such as a larger amount of an oxygenate feed under oxygenate conversion conditions, while still maintaining activity. In this discussion, the catalyst exposure lifetime refers to the amount of oxygenate a catalyst can process under oxygenate conversion conditions before the activity of the catalyst for conversion becomes substantially zero.

The molecular sieve of the invention preferably has a ratio of external surface area to internal surface area of greater than 1.20 and/or has a ratio of external acidity, as measured by collidine absorption, to internal acidity, as measured by ammonia absorption, is greater than 1.50.

In some aspects, the molecular sieve made by the process described herein in either a calcined or as-synthesized form can form agglomerates of small crystals that may have crystal sizes in the range of 0.01 to 1 μm. These small crystals can be desirable for they generally lead to greater activity. Smaller crystals can mean greater surface area which leads to a greater number of active catalytic sites per given amount of catalyst.

Optionally the zeolite contains Si and Al and has a $SiO_2:Al_2O_3$ molar ratio of greater than 2:1, optionally greater than 5:1, optionally greater than 10:1, optionally greater than 30:1, optionally greater than 100:1, and optionally greater than 150:1. The $SiO_2:Al_2O_3$ molar ratio is optionally less than 500, optionally less than 300, or optionally less than 200. While the presence of aluminium within the framework structure does contribute acidic sites to the catalyst it also is associated with a reduction in thermal stability of the zeolite. Many industrial organic feedstock conversion processes are carried out at temperatures which require the use of zeolite supports having a $SiO_2:Al_2O_3$ molar ratio of greater than 6:1 or even greater than 10:1.

The molecular sieve optionally has a degree of crystallinity of at least 80%, optionally at least 90%, preferably at least 95% and most preferably at least 98%. In one embodiment the molecular sieve is essentially pure crystalline material. The degree of crystallinity may be calculated via x-ray diffraction (XRD).

In one embodiment the molecular sieve is in as-made form and optionally comprises a structure directing agent Q, within its pores.

In an alternative embodiment the molecular sieve does not comprise a structure directing agent Q. For example, the molecular sieve may be one which can be synthesized without any structure directing agent Q.

The molecular sieve may be in calcined form. The molecular sieve crystals can be "as-synthesized" crystals that still contain the organic template, or the crystals can be calcined crystals, such as K-form molecular sieve crystals or Na-form molecular sieve crystals, or the crystals can be calcined and ion-exchanged crystals, such as H-form molecular sieve crystals.

The molecular sieve of the invention in its calcined, acid form preferably has an external acidity which is at least 1.10 times, more preferably at least 1.30 times, and in some case at least 1.50 times the external acidity of a molecular sieve made using an equivalent process except that the synthesis mixture does not include any morphology modifier L. The external acidity may be measured by collidine adsorption.

The molecular sieve of the invention may in its calcined, acid form, have an external surface area which is at least 1.10 times, more preferably at least 1.20 times, and in some cases 1.30 times the external surface area of a molecular sieve made using an equivalent process except that the synthesis mixture does not include any morphology modifier L. The external surface area may be measured by BET.

The molecular sieve of the invention in its calcined form preferably has a ratio of external surface area to internal surface area of greater than 1.20 and/or has a ratio of external acidity, as measured by collidine absorption, to internal acidity, as measured by ammonia absorption, of greater than 1.50.

The molecular sieve of the present invention or manufactured by the process of the present invention may be used as an adsorbent or as a catalyst to catalyze a wide variety of organic compound conversion processes including many of present commercial/industrial importance. Examples of preferred chemical conversion processes which can be effectively catalyzed by the zeolite of the present invention or manufactured by the process of the present invention, by itself or in combination with one or more other catalytically active substances including other crystalline catalysts, include those requiring a catalyst with acid activity or hydrogenation activity. Examples of organic conversion processes which may be catalyzed by zeolite of the present invention or manufactured by the process of the present invention include cracking, hydrocracking, isomerization, polymerization, reforming, hydrogenation, dehydrogenation, dewaxing, hydrodewaxing, adsorption, alkylation, transalkylation, dealkylation, hydrodecylization, disproportionation, oligomerization, dehydrocyclization and combinations thereof. The conversion of hydrocarbon feeds can take place in any convenient mode, for example in fluidized bed, ebullating bed, moving bed, or fixed bed reactors depending on the types of process desired.

Once the molecular sieve has been synthesized, it can be formulated into a catalyst composition by combination with other materials, such as binders and/or matrix materials that provide additional hardness or catalytic activity to the finished catalyst. These other materials can be inert or catalytically active materials.

In particular, it may be desirable to incorporate the molecular sieve of the present invention or manufactured by the process of the present invention with another material that is resistant to the temperatures and other conditions employed in organic conversion processes. Such materials include synthetic or naturally occurring zeolites as well as inorganic materials such as clays, silica and/or metal oxides such as alumina, yttria, zirconia, gallium oxide, zinc oxide and mixtures thereof. The metal oxides may be either naturally occurring or in the form of gelatinous precipitates or gels including mixtures of silica and metal oxides. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification. These binder materials are resistant to the temperatures and other conditions, e.g., mechanical attrition, which occur in various hydrocarbon conversion processes. Thus the molecular sieve of the present invention or manufactured by the process of the present invention may be used in the form of an extrudate with a binder. They are typically bound by forming a pill, sphere, or extrudate. The extrudate is usually formed by extruding the molecular sieve, optionally in the presence of a binder, and drying and calcining the resulting extrudate. Further treatments such as steaming, addition of catalytic metal or metals, and/or ion exchange may be carried out as required. The molecular sieve may optionally be bound with a binder having a surface area of at least 200 $m^2/g$, optionally at least 300 $m^2/g$.

Binders may suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions.

In addition to the foregoing materials, the molecular sieve of the present invention can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of molecular sieve and inorganic oxide matrix may vary widely, with the molecular sieve content ranging from about 1 to about 100 percent by weight and more usually, particularly when the composite is prepared in the form of extrudates, in the range of about 2 to about 95, optionally from about 20 to about 90 weight percent of the composite.

ADDITIONAL EMBODIMENTS

Additionally or alternatively, the present disclosure can include one or more of the following embodiment.

Embodiment 1

A process of preparing crystals of a molecular sieve having a framework code selected from the group consisting of MEI, TON, MRE, MWW, MFS, MOR, FAU, EMT, and MSE, the process comprising the steps of:

a. combining a source of a tetravalent element X, a morphology modifier L, water, optionally a source of hydroxide ions, optionally a structure directing agent Q, optionally a source of a trivalent element Y, optionally a source of a pentavalent element Z, optionally a source of halide ions optionally a source of alkali metal ions $M^+$ and/or a source of alkali earth metal cations $M^{2+}$, and optionally one or more other components to form a synthesis mixture;

b. heating said synthesis mixture under crystallization conditions for a time of about 1 hour to 100 days to form the crystals of the molecular sieve; and c. recovering said crystals of the molecular sieve from the synthesis mixture, wherein X=Si and the morphology modifier L is selected from the group consisting of cationic surfactants having a quaternary ammonium group comprising at least one hydrocarbyl group having at least 12 carbon atoms, nonionic surfactants, anionic surfactants, sugars and combinations thereof, and if a structure directing agent Q is present L is different from and is present in addition to the structure directing agent Q.

Embodiment 2

A process of Embodiment 1 in which the molar ratio L:X in the synthesis mixture is in the range of from 0.001 to 0.03.

Embodiment 3

A process of Embodiment 1 or 2 in which Y is present in the synthesis mixture and is Al, and the ratio of $XO_2:Y_2O_3$ is in the range of from 5 to 500.

Embodiment 4

A process of any of embodiments 1 to 3 in which the ratio $Q:(XO_2+Y_2O_3+Z_2O_5)$ is in the range of from 0.01 to 1.0.

Embodiment 5

A process of any of embodiments 1 to 4 in which the morphology modifier L is a cationic surfactant having a single quaternary ammonium group, and wherein that single ammonium group comprises at least one $C_{12}$ to $C_{30}$ alkyl group bonded to the quaternary ammonium group.

Embodiment 6

A process of any of embodiments 1 to 5 in which the morphology modifier L is a cationic surfactant having the formula (1)

$(R^1)_q(R^2)_{4-q}N^+(X^{n-})_{1/n}$      (1)

wherein each $R^1$ is independently a $C_1$-$C_6$, optionally a $C_1$ to $C_4$, hydrocarbyl group which may be linear or branched, saturated or unsaturated, preferably linear and saturated and each hydrocarbyl may include one or more heteroatoms, optionally selected from selected from oxygen, sulphur, nitrogen and halide; $R^2$ is a $C_{12}$ to $C_{30}$, optionally $C_{14}$ to $C_{30}$, optionally $C_{16}$ to $C_{30}$, optionally $C_{18}$ to $C_{30}$ hydrocarbyl which may be branched or linear, saturated or unsaturated, preferably linear and saturated, and each hydrocarbyl may include one or more heteroatoms, optionally selected from selected from oxygen, sulphur, nitrogen and halide; q is 1 or 2, preferably 1; $X^{n-}$ is an anion of valency n.

Embodiment 7

A process of any of embodiments 1 to 6 in which the morphology modifier L is a monosaccharide.

Embodiment 8

A process of any of embodiments 1 to 7 in which the morphology modifier L is an anionic surfactant.

Embodiment 9

A process of any of embodiments 1 to 8 in which the morphology modifier L is a nonionic surfactant.

Embodiment 10

A process of any of embodiments 1 to 9 in which the synthesis mixture is substantially free of water-insoluble liquid components.

Embodiment 11

A process of any of embodiments 1 to 10 which includes the step of calcining the crystals recovered in step c) to give the calcined form of the molecular sieve.

Embodiment 12

A process of any of embodiments 1 to 11 in which the molecular sieve is a zeolite selected from the group consisting of ZSM-18, ZSM-22, ZSM-48, MCM-49, ZSM-57, mordenite, cubic faujasite, hexagonal faujasite and MCM-68.

Embodiment 13

A molecular sieve having a framework code selected from the group consisting of MEI, TON, MRE, MWW, MFS, MOR, FAU, EMT, and MSE, in which the ratio of external surface area to internal surface area is greater than 1.2 and/or in which the ratio of external acidity, as measured by collidine absorption, to internal acidity, as measured by ammonia absorption, is greater than 1.5.

Embodiment 14

A molecular sieve having a framework code selected from the group consisting of MEI, TON, MRE, MWW, MFS, MOR, FAU, EMT, and MSE, and having an external surface area of at least 1.1 times the external surface area of the same molecular sieve made using an equivalent process except that the synthesis mixture does not include any morphology modifier L and/or an increased external acidity, as measured by collidine absorption, as compared to the same molecular sieve made using an equivalent process except that the synthesis mixture does not include any morphology modifier L.

Embodiment 15

A molecular sieve according to embodiment 13 or 14 as made according to the process of any of embodiments 1 to 12.

Embodiment 16

A molecular sieve according to any of embodiments 13 to 15 which is a zeolite selected from the group consisting of ZSM-18, ZSM-22, ZSM-48, MCM-49, ZSM-57, mordenite, cubic faujasite, hexagonal faujasite, and MCM-68.

Embodiment 17

A catalyst comprising the molecular sieve of any of embodiments 13 to 16, and optionally including a binder.

Embodiment 18

A hydrocarbon conversion process comprising the step of contacting a hydrocarbon feedstock with a catalyst as embodied in embodiment 17.

Embodiment 19

A hydrocarbon conversion process of embodiment 18 which is a dewaxing process or an aromatic alkylation process.

THE EXAMPLES

Syntheses of ZSM-48 were carried out according to the following procedures using hexamethonium dichloride (HMDC) as structure directing agent and different morphology modifiers.

Example 1 (Comparative). ZSM-48 Reference, No Morphology Modifier, Morphology Modifier/$SiO_2$=0.0, Morphology Modifier Present at 0 wt % of Total Mixture Dilute 1.26 g of 25% hexamethonium dichloride (HMDC) in 14.8 g of water. Stir to make sure the solution is homogeneous. Add 0.62 g of a sodium aluminate solution (7.8% $Na_2O$, 10.0% $Al_2O_3$, 82.2% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 3.95 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

$HMDC/SiO_2$=0.019

Modifier/$SiO_2$=0.000

$H_2O/SiO_2$=18.7

~5100 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Transmission Electron Microscopy (TEM) revealed that the crystals had lengths generally in the range of 30 to 50 nm and widths in the range of from 10 to 15 nm with a length:width aspect ratio of from 3 to 5.

Example 2. ZSM-48, Trimethyloctadecylammonium Bromide Morphology Modifier, Morphology Modifier/$SiO_2$=0.011, 1 wt % of Total Mixture Dilute 1.25 g of 25% hexamethonium dichloride (HMDC) in 13.7 g of water. Stir to make sure the solution is homogeneous. Add 0.61 g of a sodium aluminate solution (7.8% $Na_2O$, 10.0% $Al_2O_3$, 82.8% water) to the structure directing solution. Stir to homogenize the solution. Add 3.6 g of 10% NaOH solution to the HMDC/aluminate solution. Stir to homogenize the mixture. Add 0.74 g of colloidal beta seeds (17.2 wt % seeds) to the aluminate mixture. Add 1.28 g of 20 wt % trimethyloctadecylammonium bromide solution (cationic surfactant morphology modifier) and stir the mixture to dissolve the morphology modifier. Add 3.89 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=89.3

$OH^-/SiO_2$=0.179

$HMDC/SiO_2$=0.019

Modifier/$SiO_2$=0.011

$H_2O/SiO_2$=17.9

~5200 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 3. ZSM-48, Dodecyltrimethylammonium Bromide Morphology Modifier, Morphology Modifier/$SiO_2$=0.014, 1 wt % of Total Mixture Dilute 1.25 g of 25% hexamethonium dichloride (HMDC) in 13.7 g of water. Stir to make sure the solution is homogeneous. Add 0.61 g of a sodium aluminate solution (7.8% $Na_2O$, 10.0% $Al_2O_3$, 82.8% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 1.26 g of a 20 wt % dodecyltrimethylammonium bromide solution (cationic surfactant morphology modifier) and stir the mixture to dissolve the morphology modifier. Add 3.89 g of Ultrasil VN3 PM modified precipitated silica (92.4% $SiO_2$) to the mixture. Stir the mixture for 1 hour to prepare a homogeneous slurry. An approximate molar gel composition for the mixture is as follows:

$SiO_2/Al_2O_3$=97.2

$OH^-/SiO_2$=0.176

$HMDC/SiO_2$=0.019

Modifier/$SiO_2$=0.014

$H_2O/SiO_2$=17.9

~5200 ppm of seed
Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 4. ZSM-48, Ethylhexadecyldimethylammonium Bromide Morphology Modifier, Morphology Modifier/$SiO_2$=0.011, 1 wt % of Total Mixture Dilute 1.27 g of 25% hexamethonium dichloride (HMDC) in 13.7 g of water. Stir to make sure the solution is homogeneous. Add 0.62 g of a sodium aluminate solution (7.8% $Na_2O$, 10.0% $Al_2O_3$, 82.8% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 1.25 g of a 20 wt % ethylhexadecyldimethylammonium bromide solution (cationic surfactant morphology modifier) and stir the mixture to dissolve the morphology modifier. Add 3.89 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=98.2

$OH^-/SiO_2$=0.176

HMDC/$SiO_2$=0.019

Modifier/$SiO_2$=0.011

$H_2O/SiO_2$=17.9

~5100 ppm of seed
Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 5. ZSM-48, Cetyltrimethylammonium Bromide Morphology Modifier, Morphology Modifier/$SiO_2$=0.023, 2 wt % of Total Mixture Dilute 1.24 g of 25% hexamethonium dichloride (HMDC) in 12.5 g of water. Stir to make sure the solution is homogeneous. Add 0.61 g of a sodium aluminate solution (7.8% $Na_2O$, 10.0% $Al_2O_3$, 82.8% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 2.55 g of a 20 wt % cetyltrimethylammonium bromide solution (cationic surfactant morphology modifier) and stir the mixture to dissolve the morphology modifier. Add 3.89 g of Ultrasil VN3 PM modified precipitated silica (92.4% $SiO_2$) to the mixture. Stir the mixture for 1 hour to prepare a homogeneous slurry. An approximate molar gel composition for the mixture is as follows:

$SiO_2/Al_2O_3$=99.3

$OH^-/SiO_2$=0.174

HMDC/$SiO_2$=0.019

Modifier/$SiO_2$=0.023

$H_2O/SiO_2$=16.8

~5100 ppm of seed
Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 5B

Additional ZSM-48 crystals were synthesized using a reaction mixture similar to Example 5, but with 1 wt % CTAB instead of 2 wt %. Transmission Electron Microscopy (TEM) revealed that the crystals had a median crystal length of roughly 53 nm and an aspect ratio of roughly 2.2.

Example 6. ZSM-48, Brij L4 Morphology Modifier, Morphology Modifier/$SiO_2$=0.017, 1.6 Wt % of Total Mixture Dilute 1.24 g of 25% hexamethonium dichloride (HMDC) in 13.0 g of water. Stir to make sure the solution is homogeneous. Add 0.59 g of a sodium aluminate solution (7.5% $Na_2O$, 10.2% $Al_2O_3$, 82.3% water) to the structure directing solution. Stir to homogenize the solution. Add 3.6 g of 10% NaOH solution to the HMDC/aluminate solution. Stir to homogenize the mixture. Add 0.75 g of colloidal beta seeds (16.7 wt % seeds) to the aluminate mixture. Add 1.96 g of a 19.2 wt % Brij L4 93 solution (polyethylene glycol dodecyl ether as nonionic surfactant morphology modifier) and stir the mixture to dissolve the zeolite growth modifier. Add 3.89 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

HMDC/$SiO_2$=0.019

Modifier/$SiO_2$=0.017

$H_2O/SiO_2$=18.7

~5200 ppm of seed
Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 7. ZSM-48, Brij 93 Morphology Modifier, Morphology Modifier/$SiO_2$=0.018, 1.7 Wt % of Total Mixture Dilute 1.27 g of 25% hexamethonium dichloride (HMDC) in 12.9 g of water. Stir to make sure the solution is homogeneous. Add 0.59 g of a sodium aluminate solution (7.5% $Na_2O$, 10.2% $Al_2O_3$, 82.3% water) to the structure directing solution. Stir to homogenize the solution. Add 3.6 g of 10% NaOH solution to the HMDC/aluminate solution.

Stir to homogenize the mixture. Add 0.75 g of colloidal beta seeds (16.7 wt % seeds) to the aluminate mixture. Add 2.02 g of a 18.54 wt % Brij 93 solution (polyethylene glycol oleyl ether as nonionic surfactant morphology modifier) and stir the mixture to dissolve the zeolite growth modifier. Add 3.89 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

$HMDC/SiO_2$=0.019

$Modifier/SiO_2$=0.018

$H_2O/SiO_2$=18.7

~5200 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 8. ZSM-48, Sodium Octylsulfate Morphology Modifier, Morphology Modifier/$SiO_2$=0.026, 1.5 wt % of Total Mixture Dilute 1.27 g of 25% hexamethonium dichloride (HMDC) in 13.0 g of water. Stir to make sure the solution is homogeneous. Add 0.60 g of a sodium aluminate solution (7.5% $Na_2O$, 10.2% $Al_2O_3$, 82.3% water) to the structure directing solution. Stir to homogenize the solution. Add 3.6 g of 10% NaOH solution to the HMDC/aluminate solution. Stir to homogenize the mixture. Add 0.75 g of colloidal beta seeds (16.7 wt % seeds) to the aluminate mixture. Add 1.86 g of a 20 wt % sodium octylsulfate solution and stir the mixture to dissolve the zeolite growth modifier. Add 3.89 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

$HMDC/SiO_2$=0.019

$Modifier/SiO_2$=0.026

$H_2O/SiO_2$=18.7

~5200 ppm of seed

Seal the autoclaves and continue to stir the mixture at 300 rpm with a U-type agitator. Heat the if) mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 9 (Comparative). ZSM-48, 1,2-Hexanediol Comparative Modifier, Comparative Modifier/$SiO_2$=0.053, 1.5 wt % of Total Mixture Dilute 1.27 g of 25% hexamethonium dichloride (HMDC) in 13.1 g of water. Stir to make sure the solution is homogeneous. Add 0.60 g of a sodium aluminate solution (7.5% $Na_2O$, 10.2% $Al_2O_3$, 82.3% water) to the structure directing solution. Stir to homogenize the solution. Add 3.6 g of 10% NaOH solution to the HMDC/aluminate solution. Stir to homogenize the mixture. Add 0.75 g of colloidal beta seeds (16.7 wt % seeds) to the aluminate mixture. Add 1.86 g of a 20.1 wt % 1,2-hexandiol solution and stir the mixture to dissolve the zeolite growth modifier. Add 3.89 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

$HMDC/SiO_2$=0.019

$Modifier/SiO_2$=0.053

$H_2O/SiO_2$=18.7

~5200 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 10. ZSM-48, Trimethyloctadecylammonium Bromide Morphology Modifier, Morphology Modifier/$SiO_2$=0.021, 2.0 wt % of Total Mixture Dilute 1.26 g of 25% hexamethonium dichloride (HMDC) in 12.5 g of water. Stir to make sure the solution is homogeneous. Add 0.61 g of a sodium aluminate solution (7.8% $Na_2O$, 10.0% $Al_2O_3$, 82.2% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 2.51 g of a 20 wt % trimethyloctadecylammonium bromide (cationic surfactant morphology modifier) solution and stir the mixture to dissolve the morphology modifier. Add 3.87 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

$HMDC/SiO_2$=0.019

$Modifier/SiO_2$=0.021

$H_2O/SiO_2$=18.7

~5100 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 11. ZSM-48, Sodium Lauryl Sulfate Morphology Modifier, Morphology Modifier/SiO$_2$=0.029, 2.0 wt % of Total Mixture Dilute 1.24 g of 25% hexamethonium dichloride (HMDC) in 12.5 g of water. Stir to make sure the solution is homogeneous. Add 0.61 g of a sodium aluminate solution (7.8% Na$_2$O, 10.0% Al$_2$O$_3$, 82.2% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 2.5 g of a 20 wt % solution of sodium lauryl sulfate (anioinic surfactant morphology modifier) and stir the mixture to dissolve the morphology modifier. Add 3.90 g of Ultrasil VN3 PM modified precipitated silica (92.4% SiO$_2$) to the mixture. Stir the mixture for 15 minutes to prepare a homogeneous slurry. An approximate molar gel composition for the mixture is as follows:

SiO$_2$/Al$_2$O$_3$=100.2

OH$^-$/SiO$_2$=0.174

HMDC/SiO$_2$=0.019

Modifier/SiO$_2$=0.029

H$_2$O/SiO$_2$=18.6

~5100 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 11B

Additional ZSM-48 crystals were synthesized using a reaction mixture similar to Example 11, but with 1 wt % SLS instead of 2 wt %. Transmission Electron Microscopy (TEM) revealed that the crystals had a median crystal length of roughly 41 nm and an aspect ratio of roughly 2.0.

Example 12. ZSM-48, Sodium Lauryl Sulfate Morphology Modifier, Morphology Modifier/SiO$_2$=0.075, 5.0 wt % of Total Mixture Dilute 1.2 g of 25% hexamethonium dichloride (HMDC) in 9.1 g of water. Stir to make sure the solution is homogeneous. Add 0.59 g of a sodium aluminate solution (7.8% Na$_2$O, 10.0% Al$_2$O$_3$, 82.2% water) to the structure directing solution. Stir to homogenize the solution. Add 3.4 g of 10% NaOH solution to the HMDC/aluminate solution. Stir to homogenize the mixture. Add 0.73 g of colloidal beta seeds (17.2 wt % seeds) to the aluminate mixture. Add 6.3 g of a 20 wt % sodium lauryl sulfate (anionic surfactant morphology modifier) solution and stir the mixture to dissolve the morphology modifier. Add 3.78 g of Ultrasil VN3 PM modified precipitated silica (92.4% SiO$_2$) to the mixture. Stir the mixture for 15 minutes to prepare a homogeneous slurry. An approximate molar gel composition for the mixture is as follows:

SiO$_2$/Al$_2$O$_3$=100.9

OH$^-$/SiO$_2$=0.174

HMDC/SiO$_2$=0.019

Modifier/SiO$_2$=0.075

H$_2$O/SiO$_2$=18.6

~5100 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 13. ZSM-48, Benzylhexadecyldimethylammonium Chloride Morphology Modifier, Morphology Modifier/SiO$_2$=0.016, 1.5 wt % of Total Mixture Dilute 1.24 g of 25% hexamethonium dichloride (HMDC) in 13.1 g of water. Stir to make sure the solution is homogeneous. Add 0.61 g of a sodium aluminate solution (7.8% Na$_2$O, 10.0% Al$_2$O$_3$, 82.2% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 1.88 g of a 20 wt % solution of benzylhexadecyldimethylammonium chloride (cationic surfactant morphology modifier) and stir the mixture to dissolve the morphology modifier. Add 3.89 g of Ultrasil VN3 PM modified precipitated silica (92.4% SiO$_2$) to the mixture. Stir the mixture for 15 minutes to prepare a homogeneous slurry. An approximate molar gel composition for the mixture is as follows:

SiO$_2$/Al$_2$O$_3$=100.0

OH$^-$/SiO$_2$=0.175

HMDC/SiO$_2$=0.019

Modifier/SiO$_2$=0.016

H$_2$O/SiO$_2$=18.7

~5100 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 14. ZSM-48 Dihexadecyldimethylammonium Bromide Morphology Modifier, Morphology Modifier/SiO$_2$=0.012, 1.5 wt % of Total Mixture Dilute 1.24 g of 25% hexamethonium dichloride (HMDC) in 13.1 g of water. Stir to make sure the solution is homogeneous. Add 0.61 g of a sodium aluminate solution (7.8% Na$_2$O, 10.0% Al$_2$O$_3$, 82.2% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 1.86 g of a 20 wt % solution of dihexadecyldimethylammonium bromide (cationic surfactant morphology modifier) and stir the mixture to dissolve the morphology modifier. Add 3.89 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

$HMDC/SiO_2$=0.019

$Modifier/SiO_2$=0.012

$H_2O/SiO_2$=18.7

~5100 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Example 15. ZSM-48 Lithium Dodecyl Sulfate Morphology Modifier, Morphology Modifier/$SiO_2$=0.023, 1.5 wt % of Total Mixture Dilute 1.24 g of 25% hexamethonium dichloride (HMDC) in 13.1 g of water. Stir to make sure the solution is homogeneous. Add 0.61 g of a sodium aluminate solution (7.8% $Na_2O$, 10.0% $Al_2O_3$, 82.2% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 1.86 g of a 20 wt % solution of lithium dodecyl sulfate (anionic surfactant morphology modifier) and stir the mixture to dissolve the morphology modifier. Add 3.89 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

$HMDC/SiO_2$=0.019

$Modifier/SiO_2$=0.023

$H_2O/SiO_2$=18.7

~5100 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Transmission Electron Microscopy (TEM) revealed that the crystals had lengths generally in the range of 30 to 60 nm and widths in the range of around 30 nm with a length:width aspect ratio range of from 1 to 2.

Example 16. ZSM-48 Pluronic EO-PO-EO Morphology Modifier, Morphology Modifier/$SiO_2$=0.0007, 1.0 wt % of Total Mixture Dilute 1.25 g of 25% hexamethonium dichloride (HMDC) in 13.7 g of water. Stir to make sure the solution is homogeneous. Add 0.61 g of a sodium aluminate solution (7.8% $Na_2O$, 10.0% $Al_2O_3$, 82.2% water) to the structure directing solution. Stir to homogenize the solution. Add 3.6 g of 10% NaOH solution to the HMDC/aluminate solution. Stir to homogenize the mixture. Add 0.73 g of colloidal beta seeds (17.2 wt % seeds) to the aluminate mixture. Add 1.24 g of a 20 wt % solution of Pluronic EO-PO-EO tri-block co-polymer) nonionic surfactant morphology modifier) and stir the mixture to dissolve the morphology modifier. Add 3.91 g of Ultrasil VN3 PM modified precipitated silica (92.4% $SiO_2$) to the mixture. Stir the mixture for 15 minutes to prepare a homogeneous slurry. An approximate molar gel composition for the mixture is as follows:

$SiO_2/Al_2O_3$=100.0

$OH^-/SiO_2$=0.175

$HMDC/SiO_2$=0.019

$Modifier/SiO_2$=0.0007

$H_2O/SiO_2$=18.7

~5100 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

The following syntheses of MCM-49 were carried out using hexamethyleneimine (HMI) as structure directing agent according to the following procedures.

Example 17. MCM-49 Reference No Morphology Modifier, Morphology Modifier/$SiO_2$=0.000, 0 wt % of Total Mixture Dilute 3.54 g of 40 wt % solution of aluminum sulfate octahydrate in 12.0 g of water. Add 4.1 g of 20% NaOH solution to the aluminum sulfate solution. Stir to homogenize the mixture. Add 3.46 g of Ultrasil VN3 PM modified precipitated silica (92.4% $SiO_2$) to the sodium aluminate solution. Stir the mixture until the slurry appears to be homogeneous. Add 1.86 g of hexamethyleneimine (HMI) to the slurry. Stir the mixture for 10 minutes to prepare a homogeneous slurry. An approximate molar gel composition for the mixture is as follows:

$SiO_2/Al_2O_3$=25.0

$OH^-/SiO_2$=0.390

$HMI/SiO_2$=0.350

$Modifier/SiO_2$=0.000

$H_2O/SiO_2$=18.5

Seal the autoclaves and continue to stir the mixture at 360 rpm with a U-type agitator. Heat the mixture to 143° C. (20° C./hr. ramp rate) and hold for 5 days. Isolate the solid via vacuum filtration and wash with 3 volumes of water. Dry the material in an oven at 120° C. X-ray diffraction indicates that the powder is MCM-49/MCM-22 structure type.

Example 18. MCM-49 Cetyltrimethylammonium Bromide Morphology Modifier, Morphology Modifier/SiO$_2$=0.013, 1 wt % of Total Mixture Dilute 3.51 g of 40 wt % solution of aluminum sulfate octahydrate in 10.9 g of water. Add 4.1 g of 20% NaOH solution to the aluminum sulfate solution. Stir to homogenize the mixture. Add 3.42 g of Ultrasil VN3 PM modified precipitated silica (92.4% SiO$_2$) to the sodium aluminate solution. Stir the mixture until the slurry appears to be homogeneous. Add 1.85 g of hexamethyleneimine (HMI) to the slurry. Add 1.26 g of 20 wt % cetyltrimethylammonium bromide (cationic surfactant morphology modifier) to the slurry. Stir the mixture for 10 minutes to prepare a homogeneous slurry. An approximate molar gel composition for the mixture is as follows:

SiO$_2$/Al$_2$O$_3$=25.0

OH$^-$/SiO$_2$=0.390

HMI/SiO$_2$=0.350

Modifier/SiO$_2$=0.013

H$_2$O/SiO$_2$=19.6

Seal the autoclaves and continue to stir the mixture at 360 rpm with a U-type agitator. Heat the mixture to 143° C. (20° C./hr. ramp rate) and hold for 5 days. Isolate the solid via vacuum filtration and wash with 3 volumes of water. Dry the material in an oven at 120° C. X-ray diffraction indicates that the powder is MCM-49/MCM-22 structure type.

Example 19. MCM-49 Sodium Lauryl Sulfate Morphology Modifier, Morphology Modifier/SiO$_2$=0.016, 1 wt % of Total Mixture Dilute 3.51 g of 40 wt % solution of aluminum sulfate octahydrate in 10.9 g of water. Add 4.1 g of 20% NaOH solution to the aluminum sulfate solution. Stir to homogenize the mixture. Add 3.42 g of Ultrasil VN3 PM modified precipitated silica (92.4% SiO$_2$) to the sodium aluminate solution. Stir the mixture until the slurry appears to be homogeneous. Add 1.85 g of hexamethyleneimine (HMI) to the slurry. Add 1.26 g of 20 wt % sodium lauryl sulfate (anionic surfactant morphology modifier) to the slurry. Stir the mixture for 10 minutes to prepare a homogeneous slurry. An approximate molar gel composition for the mixture is as follows:

SiO$_2$/Al$_2$O$_3$=25.0

OH$^-$/SiO$_2$=0.390

HMI/SiO$_2$=0.350

Modifier/SiO$_2$=0.016

H$_2$O/SiO$_2$=19.6

Seal the autoclaves and continue to stir the mixture at 360 rpm with a U-type agitator. Heat the mixture to 143° C. (20° C./hr. ramp rate) and hold for 5 days. Isolate the solid via vacuum filtration and wash with 3 volumes of water. Dry the material in an oven at 120° C. X-ray diffraction indicates that the powder is MCM-49/MCM-22 structure type.

Example 20. ZSM-48 Fructose Morphology Modifier, Modifier/SiO$_2$=0.020, 1.0 wt. % of Total Mixture Dilute 1.39 g of 56% hexamethonium dichloride (HMDC) in 14.4 g of water. Stir to make sure the solution is homogeneous. Add 1.42 g of a sodium aluminate solution (20% NaOH, 7.8% Al(OH)$_3$, 72.2% water) to the structure directing solution. Stir to homogenize the solution. Add 2.6 g of 10% NaOH solution to the HMDC/aluminate solution. Stir to homogenize the mixture. Add 0.03 g of ZSM-48 seeds to the aluminate mixture. Add 0.63 g of a 39.7% solution of fructose and stir to homogenize the mixture. Add 4.62 g of Ultrasil VN3 PM modified precipitated silica (92.4% SiO$_2$) to the mixture. Stir the mixture for 15 minutes to prepare a homogeneous slurry. An approximate molar gel composition for the mixture is as follows:

SiO$_2$/Al$_2$O$_3$=99.9

OH$^-$/SiO$_2$=0.190

HMDC/SiO$_2$=0.040

Modifier/SiO$_2$=0.020

H$_2$O/SiO$_2$=14.9

~1000 ppm of seed

Seal the autoclaves and continue to stir the mixture at 300 rpm with a U-type agitator. Heat the mixture to 160° C. (20° C./hr. ramp rate) and hold for 28 hours. Isolate the solid via vacuum filtration and wash with 3 volumes of water. Dry the material in an oven at 120° C. X-ray diffraction indicates that the powder is ZSM-48.

Post-Synthesis Treatments and Measurements

The samples of molecular sieve made according to Examples 1 to 20 above were subjected to the following treatments.

After crystallization is complete and the material is determined to be crystalline via XRD, the crystal is ion-exchanged with NH$_4$NO$_3$ twice, washed with water, and dried in an oven at 120° C. The ammonium form of the powder is then calcined in air at 550° C. for 2 hours to produce the acid form of the zeolite crystal.

The acid form of the crystal is then characterized using collidine adsorption to evaluate the acidity of the catalyst. The Nitrogen BET technique is used to determine the surface area, total and external, and pore volume of the crystal. This data is collected for the reference material and each inventive modified material and the ratios of External Surface Area and Collidine absorption of each inventive example to the reference example of the same zeolite are shown in Table 3 to demonstrate the changes in acidity and external surface area of the modified crystals caused by the presence of the morphology modifier in the synthesis mixture.

The BET analysis was carried out as described in S. J. Gregg, K. S. W. Sing, "Adsorption, Surface Area and Porosity", 1st ed., Academic Press, N.Y. (1967) pp 30-31.

Ammonia and Collidine absorption tests were carried out generally as described in J. Phys. Chem. B, 2002, 106 (2), pp 395-400 (note that the equipment was in some cases slightly different, but the measurements were carried out on thermogravimetric balances in all cases).

TABLE 3

Collidine absorption and External SA results for Examples 1 to 20.

| Example | Zeolite | Modifier | Collidine/ Collidine of reference | External SA/ External SA of reference |
|---|---|---|---|---|
| 1 | ZSM-48 | none | 1.00 | 1.00 |
| 2 | ZSM-48 | trimethyloctadecyl-ammonium bromide | 1.76 | 1.45 |
| 3 | ZSM-48 | dodectyltrimethyl-ammonium bromide | 1.95 | 1.34 |
| 4 | ZSM-48 | ethylhexadecyldimethyl-ammonium bromide | 1.52 | 1.40 |
| 5 | ZSM-48 | cetyltrimethylammonium bromide | 1.80 | 1.93 |
| 6 | ZSM-48 | Brij L4 | 1.04 | 1.10 |
| 7 | ZSM-48 | Brij 93 | 1.08 | 1.20 |
| 8 | ZSM-48 | sodium octylsulfate | 1.01 | 1.20 |
| 9 | ZSM-48 | 1,2-hexanediol | 1.00 | 1.00 |
| 10 | ZSM-48 | trimethyloctadecyl-ammonium bromide | 1.66 | 1.73 |
| 11 | ZSM-48 | sodium lauryl sulfate | 0.98 | 0.90 |
| 12 | ZSM-48 | sodium lauryl sulfate | 0.92 | 0.90 |
| 13 | ZSM-48 | benzylhexadecyldimethyl-ammonium chloride | 1.14 | 1.10 |
| 14 | ZSM-48 | dihexadecyldimethyl-ammonium bromide | 1.00 | 1.10 |
| 15 | ZSM-48 | lithium dodecyl sulfate | 0.72 | 0.80 |
| 16 | ZSM-48 | Pluronic EO-PO-EO | 1.17 | 1.10 |
| 17 | MCM-49 | none | 1.00 | 1.00 |
| 18 | MCM-49 | cetyltrimethylammonium bromide | 1.25 | 1.53 |
| 19 | MCM-49 | sodium lauryl sulfate | 1.06 | 1.22 |
| 20 | ZSM-48 | fructose | — | 1.17 |

The results in Table 3 show that the use of 1,2-hexanediol, which is not a morphology modifier as described herein, no effect was seen on either collidine absorption or external surface area, which were the same as for the reference ZSM-48 of comparative Example 1.

For inventive Examples 2-8, 10-16, 18 and 19 the presence of the morphology modifier had a noticeable effect on the collidine absorption and/or the External SA as compared to the synthesis of the reference material with no morphology modifier present. In Examples 11 and 12 the recorded collidine absorption and External SA values were lower than for the reference synthesis of the same zeolite with no morphology modifier present, but were within 10% and so may have been due to experimental error. For Example 15, the collidine absorption and external SA results were lower than for the reference material. In this case, TEM results showed that the aspect ratio of the crystals made in the presence of lithium dodecyl sulfate as morphology modifier was significantly reduced as compared to the reference ZSM-48, principally because the width of the crystals increased compared to the reference materials. In ZSM-48 the one-dimensional channels in the framework run lengthways through the crystal, and so an increase in the width of the crystal compared to the length may make those channels more available to incoming reactant molecules.

Examples 21 to 24—Catalyst Lifetime for Small Crystal Size 1-Dimensional Zeolite Catalysts For catalysts based on a 1-dimensional zeolite, the catalyst exposure lifetime can be improved by reducing the crystal size of the zeolites along the direction of the pore channels. This can be accomplished by modifying the synthesis conditions for making the zeolite, by using a zeolite growth modifier (ZGM) in the synthesis mixture, or by another method that allows the crystal size to be reduced or minimized along the direction of the pore channels.

A small size crystal for a 1-dimensional zeolite can correspond to a crystal length along the direction of the pore channels of 90 nm or less, or 70 nm or less, or 50 nm or less, or 45 nm or less, such as down to 20 nm or possibly still smaller. In such aspects, the crystals can have an aspect ratio, defined as the ratio of the length along the pore channel direction versus a length along an orthogonal direction, of 4.0 or less, or 3.0 or less, or 2.5 or less, or 2.0 or less, such as down to 1.0 or possibly still lower. It is noted that the length of the crystal along the pore channel direction for some 1-dimensional zeolites, such as ZSM-48, can typically correspond to the longest direction for the crystal.

A methanol conversion catalyst with an increased catalyst exposure lifetime can be valuable in a variety of contexts. For a fixed bed system (such as a trickle bed reactor), increasing the catalyst lifetime can allow for longer run lengths at a given thickness for the catalyst bed and/or similar run lengths with a reduced amount of catalyst. For a system where continuous catalyst regeneration can be performed, such as a fluidized bed reactor or a moving bed reactor, increasing the catalyst lifetime can allow for a reduction in the rate of catalyst removal from the system and corresponding addition of fresh make-up catalyst. In this discussion, the catalyst exposure lifetime refers to the amount of oxygenate a catalyst can process under oxygenate conversion conditions before the activity of the catalyst for conversion becomes substantially zero.

To investigate crystal size effects, ZSM-48 catalysts were synthesized at two different silica to alumina ratios (roughly 70:1 and 90:1) and different lengths along the direction of the pore channels (roughly 60-70 nm or greater than 100 nm). More generally, the size effect demonstrated in this example is believed to be suitable for use with various 1-dimensional 10-member ring zeolites, at silicon to aluminum ratios of 30 to 100 and with hexane cracking activities of 15 or more (as defined in U.S. Pat. No. 3,354,078, incorporated herein by reference for the limited purpose of describing the hexane cracking activity test).

The synthesis mixtures for preparing the catalysts are shown in Table 3. The synthesis mixtures are described based on weight ratios for most components, with a weight in the mixture provided for the seeds. For each synthesis mixture, the silica to alumina ratio, crystal length (along the pore channel direction), and the aspect ratio (AR) are listed.

TABLE 3

Synthesis Mixtures for ZSM-48 Catalysts with Various Aspect Ratios

| ZSM-48 Si/Al$_2$ ratio | 90:1 (138 nm, AR = 7) Catalyst A/ Example 21 | 90:1 (66 nm, AR = 3) Catalyst B/ Example 22 | 70:1 (110 nm, AR = 7) Catalyst C/ Example 23 | 70:1 (61 nm, AR = 3) Catalyst D/ Example 24 |
|---|---|---|---|---|
| Si/Al$_2$ | 106 | 106 | 76.1 | 76.5 |
| H$_2$O/Si | 20.15 | 20.15 | 15.08 | 14.98 |

TABLE 3-continued

Synthesis Mixtures for ZSM-48 Catalysts with Various Aspect Ratios

| ZSM-48 Si/Al$_2$ ratio | 90:1 (138 nm, AR = 7) Catalyst A/ Example 21 | 90:1 (66 nm, AR = 3) Catalyst B/ Example 22 | 70:1 (110 nm, AR = 7) Catalyst C/ Example 23 | 70:1 (61 nm, AR = 3) Catalyst D/ Example 24 |
|---|---|---|---|---|
| OH−/Si | 0.17 | 0.17 | 0.156 | 0.154 |
| Na+/Si | 0.17 | 0.17 | 0.129 | 0.126 |
| SDA/Si | 0.035 | 0.020 | 0.026 | 0.018 |
| Seeds (zeolite Beta) | 0.5 wt % | 0.5 wt % | 0.5 wt % | 0.5 wt % |

For the 90:1 ZSM-48 synthesis mixtures, a mixture was prepared from water, hexamethonium chloride (56% solution), a commercially available Ultrasil silica (available from Degussa), sodium aluminate solution (45%), TEAOH solution (35%), 50% sodium hydroxide solution, and seed. The mixture was reacted at 320° F. (160° C.) with stirring at 250 RPM for 48 hours. The product was filtered, washed with deionized (DI) water and dried at 250° F. (120° C.). The XRD pattern of the as-synthesized material showed the typical pure phase of ZSM-48 topology. The SEM of the as-synthesized material shows that the material was composed of agglomerates of crystals. For the crystals with an aspect ratio of roughly 7, the crystals had needle-like morphology, while the crystals with an aspect ratio of roughly 3 had an irregular morphology.

For the 70:1 ZSM-48 synthesis mixtures, a mixture was prepared from water, hexamethonium chloride (56% solution), a commercially available Ultrasil silica, sodium aluminate solution (43%), TEAOH solution (35%), 50% sodium hydroxide solution, and seed. The mixture was reacted at 340° F. (~170° C.) with stirring at 250 RPM for 24 hours. The product was filtered, washed with deionized (DI) water and dried at 250° F. (120° C.). The XRD pattern of the as-synthesized material showed the typical pure phase of ZSM-48 topology. The SEM of the as-synthesized material shows that the material was composed of agglomerates of crystals. For the crystals with an aspect ratio of roughly 7, the crystals had needle-like morphology, while the crystals with an aspect ratio of roughly 3 had an irregular morphology.

After synthesis, the catalysts were formulated with an alumina binder to make catalyst particles with 80 wt % zeolite, 20 wt % binder.

For Catalyst A (90:1, length=138 nm), the bound catalyst had an Alpha value of 90, a hexane cracking activity of ~56, a median pore size of 9.0 Angstroms, a BET surface area of 298 m$^2$/g (174 m$^2$/g of micropore surface area), an aspect ratio of 7, and a median crystal length of 138 nm.

For Catalyst B (90:1, length=66 nm), the bound catalyst had an Alpha value of 100, a hexane cracking activity of ~55, a median pore size of 6.5 Angstroms, a BET surface area of 275 m$^2$/g (165 m$^2$/g of micropore surface area), an aspect ratio of 3, and a median crystal length of 66 nm.

For Catalyst C (70:1, length=110 nm), the bound catalyst had an Alpha value of 120, a hexane cracking activity of ~52, a median pore size of 20.3 Angstroms, a BET surface area of 323 m$^2$/g (171 m$^2$/g of micropore surface area), an aspect ratio of 7, and a median crystal length of 110 nm.

For Catalyst D (70:1, length=61 nm), the bound catalyst had an Alpha value of 140, a hexane cracking activity of ~49, a median pore size of 14.4 Angstroms, a BET surface area of 324 m$^2$/g (169 m$^2$/g of micropore surface area), an aspect ratio of 3, and a median crystal length of 61 nm.

In addition to Catalysts A-D, a fifth ZSM-48 catalyst with a silica to alumina ratio of roughly 70:1 and a median crystal length of less than 90 nm was also synthesized. This catalyst is referred to as a "reference" ZSM-48 catalyst. This reference ZSM-48 catalyst is similar to ZSM-48 catalysts that were described and used in U.S. Patent Application Publication 2018/0201843.

The catalysts were tested in an isothermal fixed-bed reactor without recycle, although recycle is possible and may be desirable as it can further extend catalyst cycle length or modify overall yields. This reactor configuration is illustrative and should not be considered limiting, as moving or fluid bed operation may be preferable. In this example, pure methanol was used as a model feed, but co-feeds such as water, oxygenates (e.g. ethanol, DME) olefins, paraffins, and aromatics are possible and may even be desirable. The conditions for testing were 2 h$^{-1}$ WHSV (on a zeolite basis), a temperature of 450° C., and a pressure of ~100 kPa-g.

Figure 2:
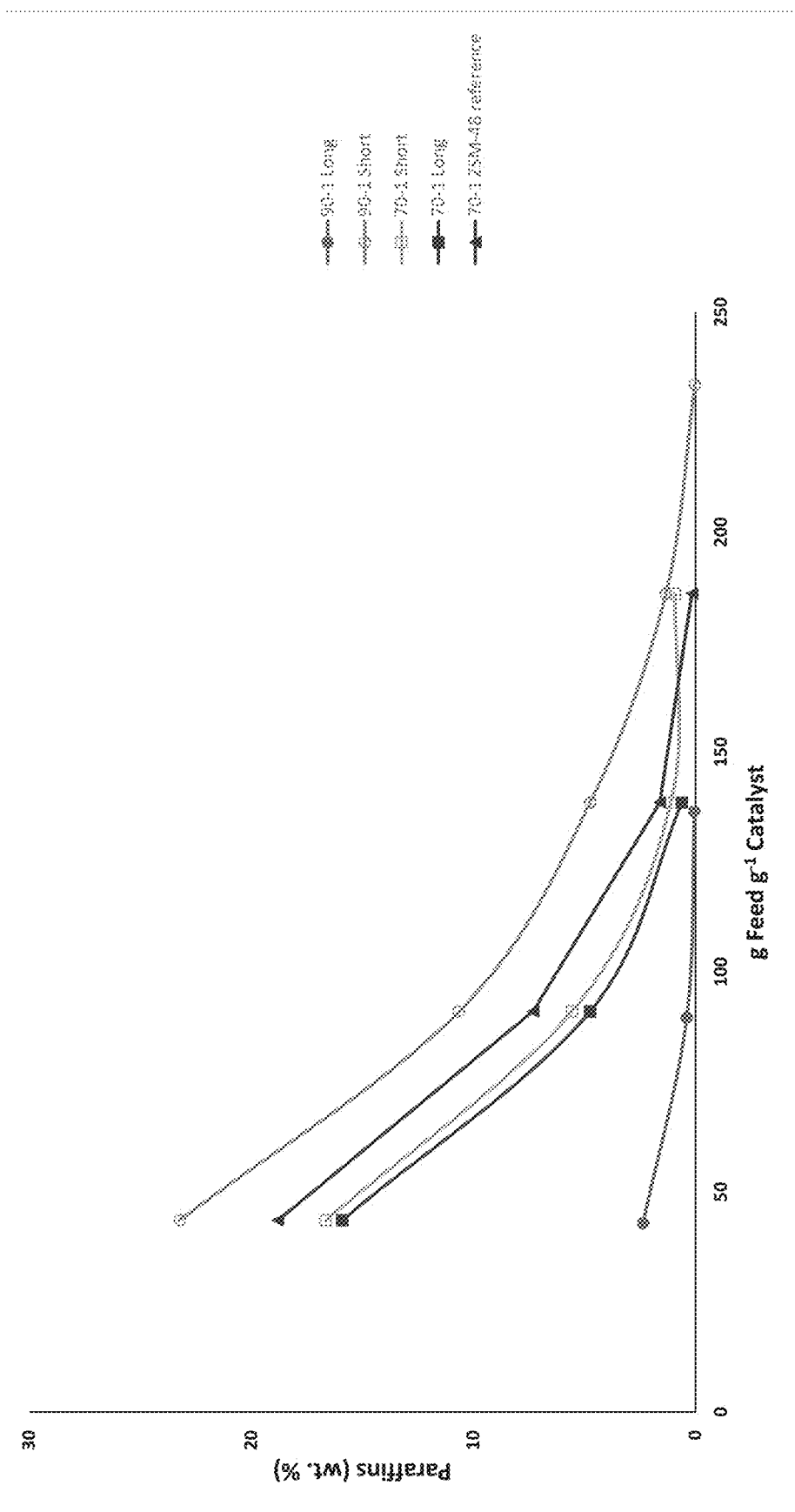
FIG. 2 shows paraffin yield versus the amount of methanol exposure for various ZSM-48 catalysts.
Figure 3:
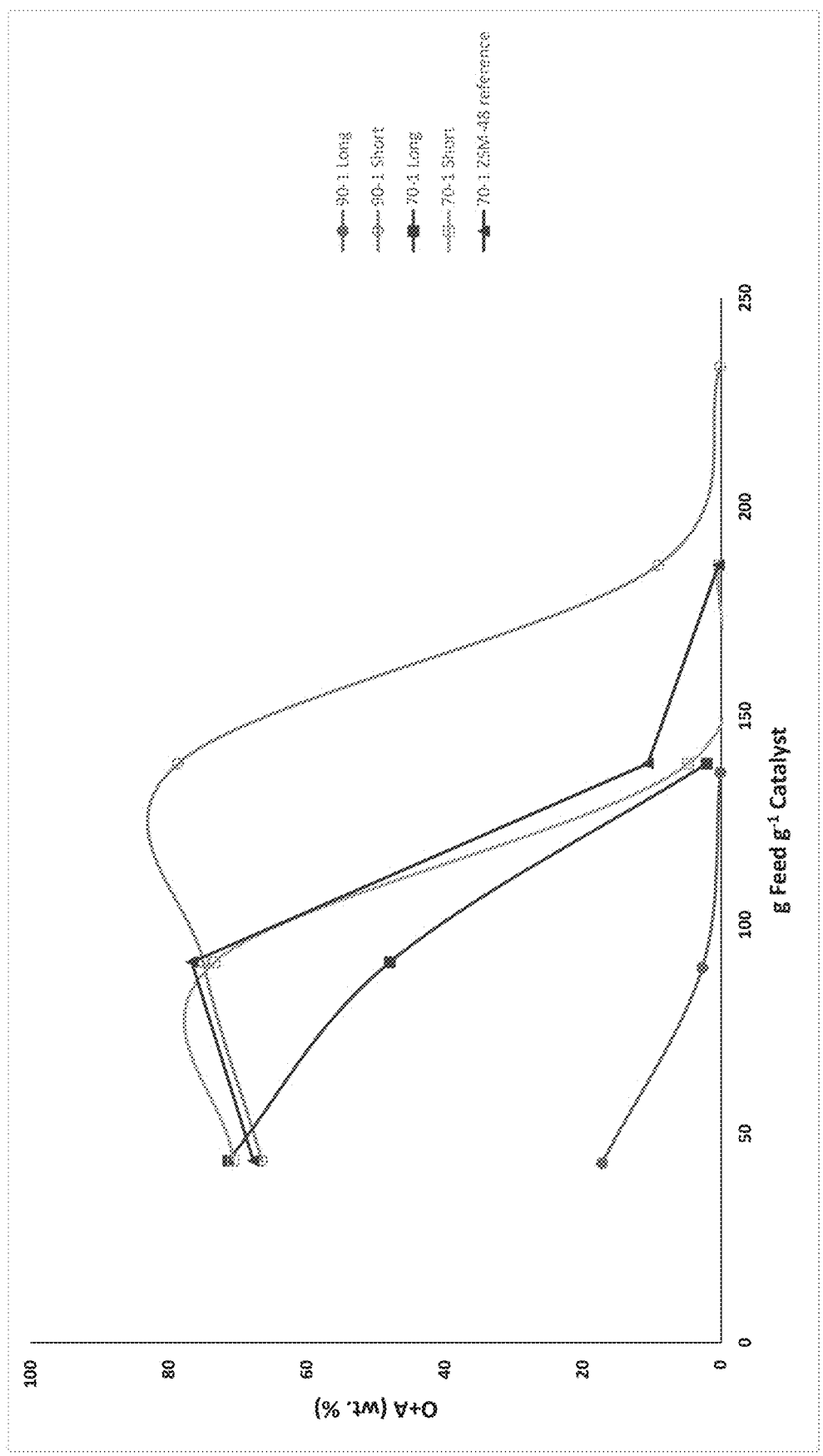
FIG. 3 shows combined olefin plus aromatics yield versus the amount of methanol exposure for various ZSM-48 catalysts.
Figure 4:
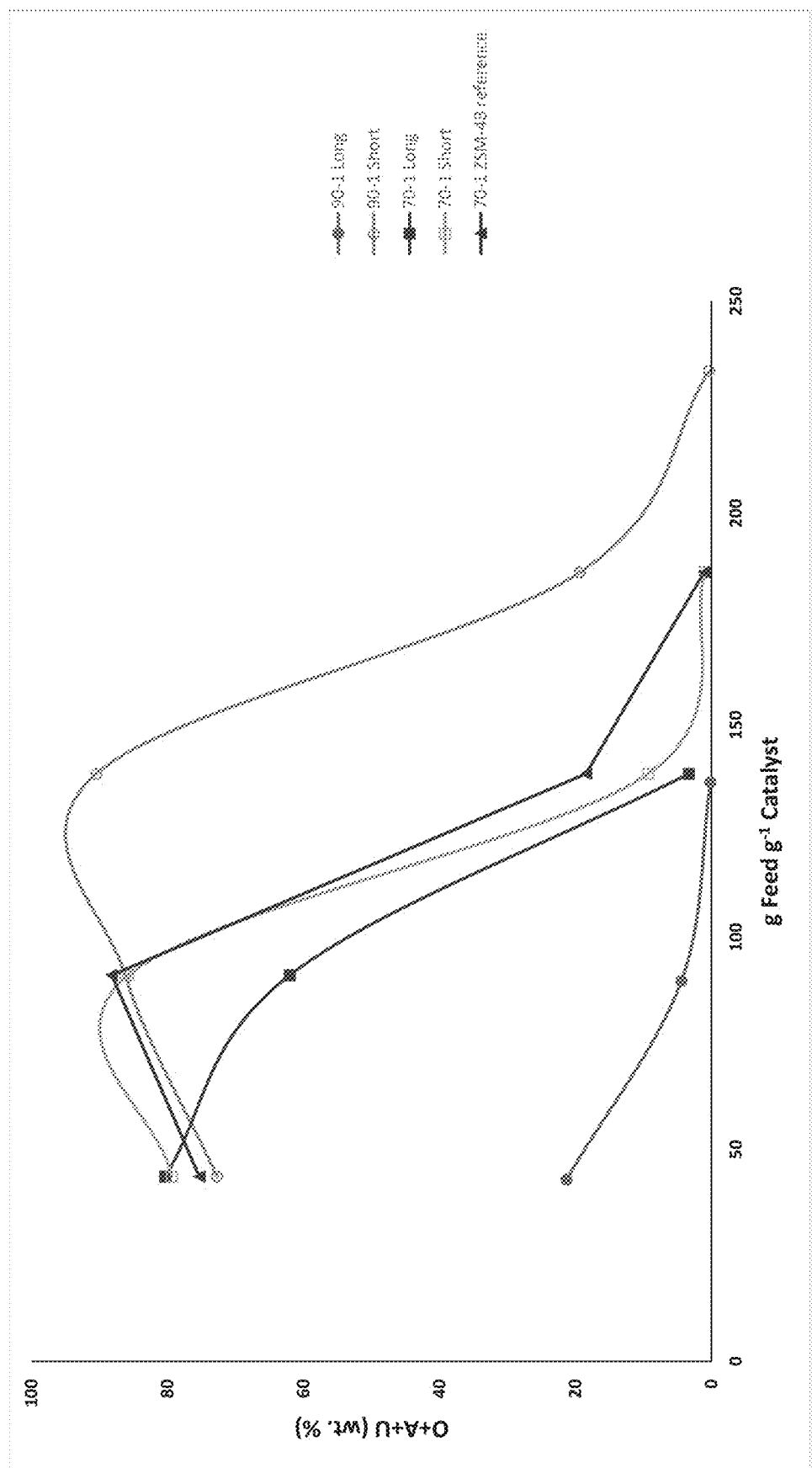
FIG. 4 shows combined olefin, aromatics, and unknowns yield versus the amount of methanol exposure for various ZSM-48 catalysts.

FIGS. 1 to 4 show results from the methanol conversion tests. FIG. 1 shows olefin yield relative to the amount of methanol exposed to the catalyst (g MeOH/g catalyst). FIG. 2 shows paraffin yield relative to the methanol exposure. FIG. 3 shows combined olefin and aromatics yield relative to the methanol exposure. FIG. 4 shows combined olefin, aromatics, and unknowns yield relative to the methanol exposure. The "unknowns" in FIG. 4 are believed to mostly correspond to iso-olefins that include 6 carbons or more. Thus, the "unknowns" likely correspond to compounds that have relatively high octane values.

As shown in FIG. 1, modifying the aspect ratio of the 90:1 ZSM-48 catalyst had a substantial impact on both yield and catalyst lifetime. This is due in part to the relatively low yield at any exposure for the 90:1 ZSM-48 with the aspect ratio of 7. However, the 90:1 ZSM-48 with the aspect ratio of 3 and a crystal length of less than 75 nm appeared to have a longer lifetime than either of the 70:1 ZSM-48 catalysts. For the 70:1 catalysts, the lower aspect ratio catalyst had a somewhat higher peak yield of olefins, but the amount of catalyst exposure lifetime increase was modest. The catalyst exposure lifetime for the reference catalyst was similar to the 70:1 ZSM-48 catalyst with the aspect ratio of 3 and a crystal length of roughly 61 nm.

With regard to paraffin yields, FIG. 2 shows that the 90:1 ZSM-48 crystals with an aspect ratio of 7 had low activity generally, while the 90:1 ZSM-48 with an aspect ratio of 3 had the highest paraffin yields at all exposures. The paraffin yields for the 70:1 catalysts were mostly similar, but the 70:1 ZSM-48 with an aspect ratio of 3 appeared to have a longer lifetime before having paraffin yield go to substantially 0. As in FIG. 1, the catalyst exposure lifetime of the reference catalyst was similar to the catalyst exposure lifetime for the 70:1 catalyst having an aspect ratio of 3 and a crystal length of roughly 61 nm.

FIG. 3, which shows combined olefin and aromatic yields, also shows trends similar to those in FIG. 1. Thus, FIG. 3 shows a substantial yield increase for 90:1 ZSM-48 with an aspect ratio of 3, while the 70:1 ZSM-48 with an aspect ratio of 3 provides only a modest increase in lifetime relative to the higher aspect ratio 70:1 ZSM-48. FIG. 4, which shows combined olefin, aromatic, and "unknown" yield, also shows similar trends to the data in FIG. 1 and FIG. 3.

To further investigate the benefit of small crystal size for catalyst exposure lifetime of 1-dimensional zeolites, the catalysts from Example 5B (CTAB) and Example 11B (SLS) were exposed to a methanol feed under the reaction conditions and reactor configuration described above. Additionally, ZSM-48 crystals made using a method similar to Example 5B or Example 11B, but with 1 wt % sodium sulfate as a crystal growth modifier, were also tested. The data from the reference catalyst from FIGS. 1-4 is also shown for comparison.

The catalyst made using sodium sulfate as the growth modifier had an Alpha value of 130, a BET surface area of 280 m$^2$/g (167 m$^2$/g of micropore surface area), an aspect ratio of 2.4, and a median crystal length of 49 nm. The catalyst made using CTAB as the growth modifier (Example 5B) had an Alpha value of 120, a BET surface area of 327 m$^2$/g (176 m$^2$/g of micropore surface area), an aspect ratio of 2.2, and a median crystal length of 53 nm. The catalyst made using SLS as the growth modifier (Example 11B) had an Alpha value of 120, a BET surface area of 281 m$^2$/g (167 m$^2$/g of micropore surface area), an aspect ratio of 2.0, and a median crystal length of 41 nm.

Figure 5:
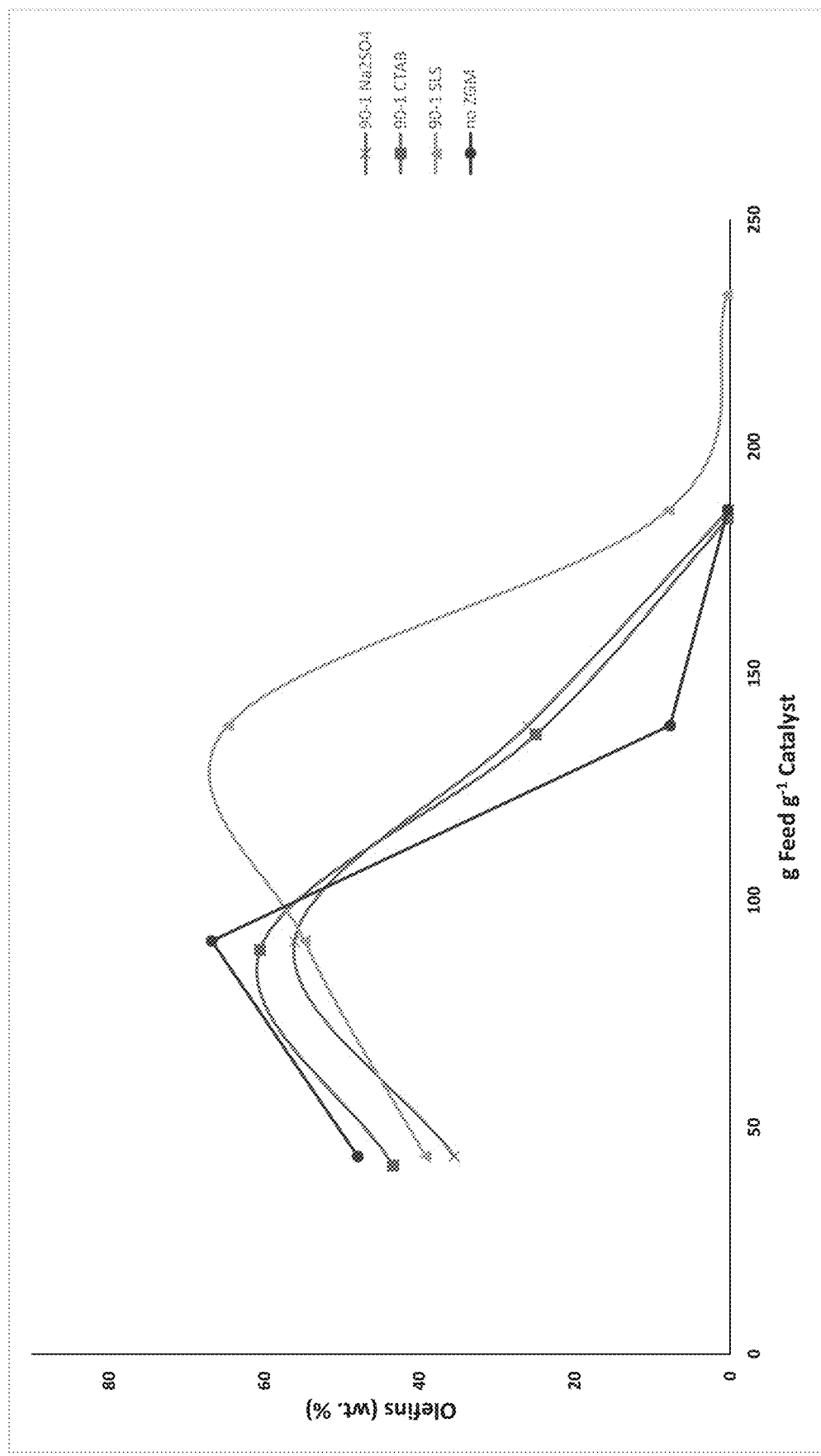
FIG. 5 shows olefin yield versus the amount of methanol exposure for ZSM-48 catalysts synthesized with various zeolite growth modifiers.
Figure 6:
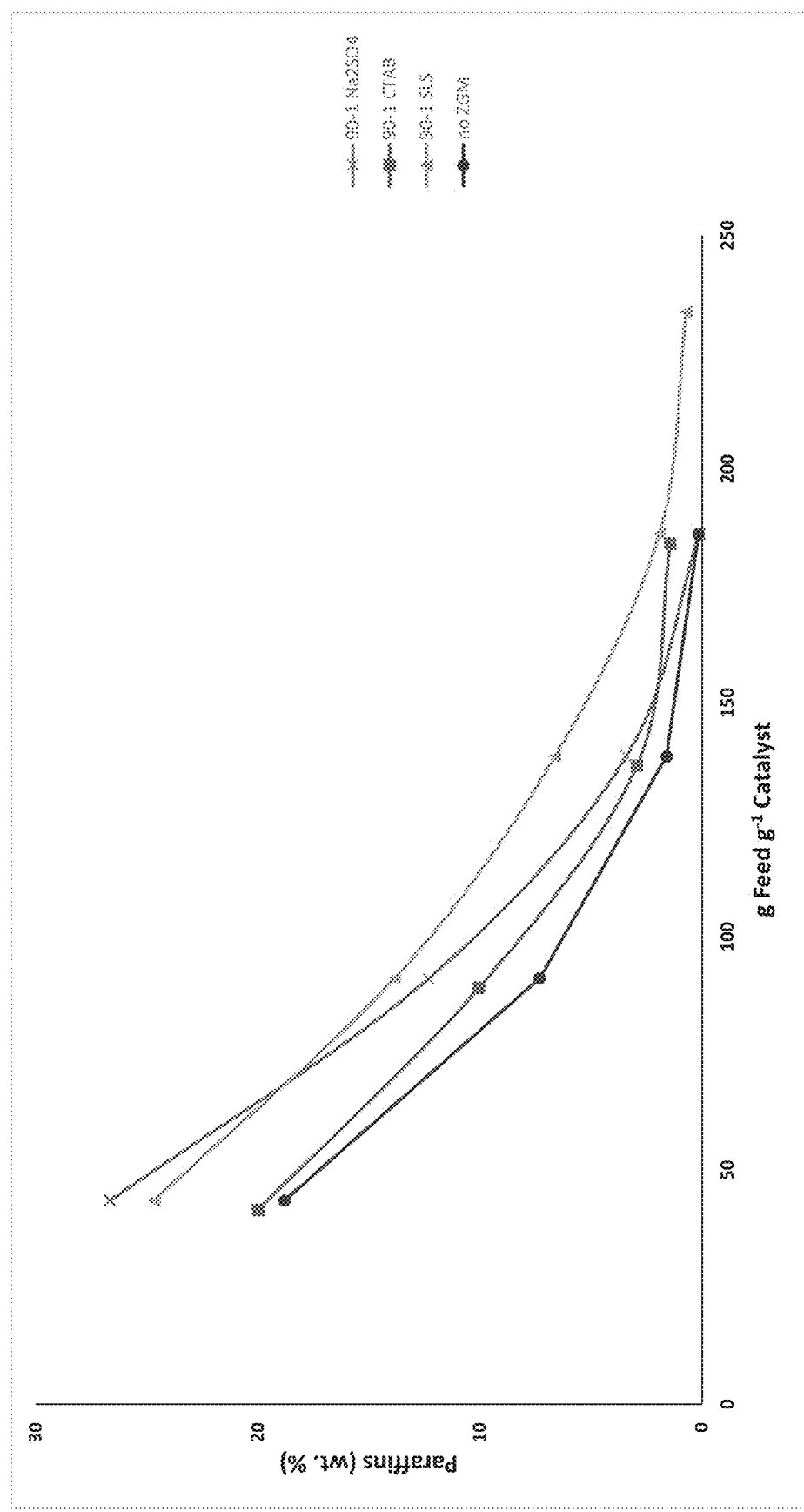
FIG. 6 shows paraffin yield versus the amount of methanol exposure for ZSM-48 catalysts synthesized with various zeolite growth modifiers.
Figure 7:
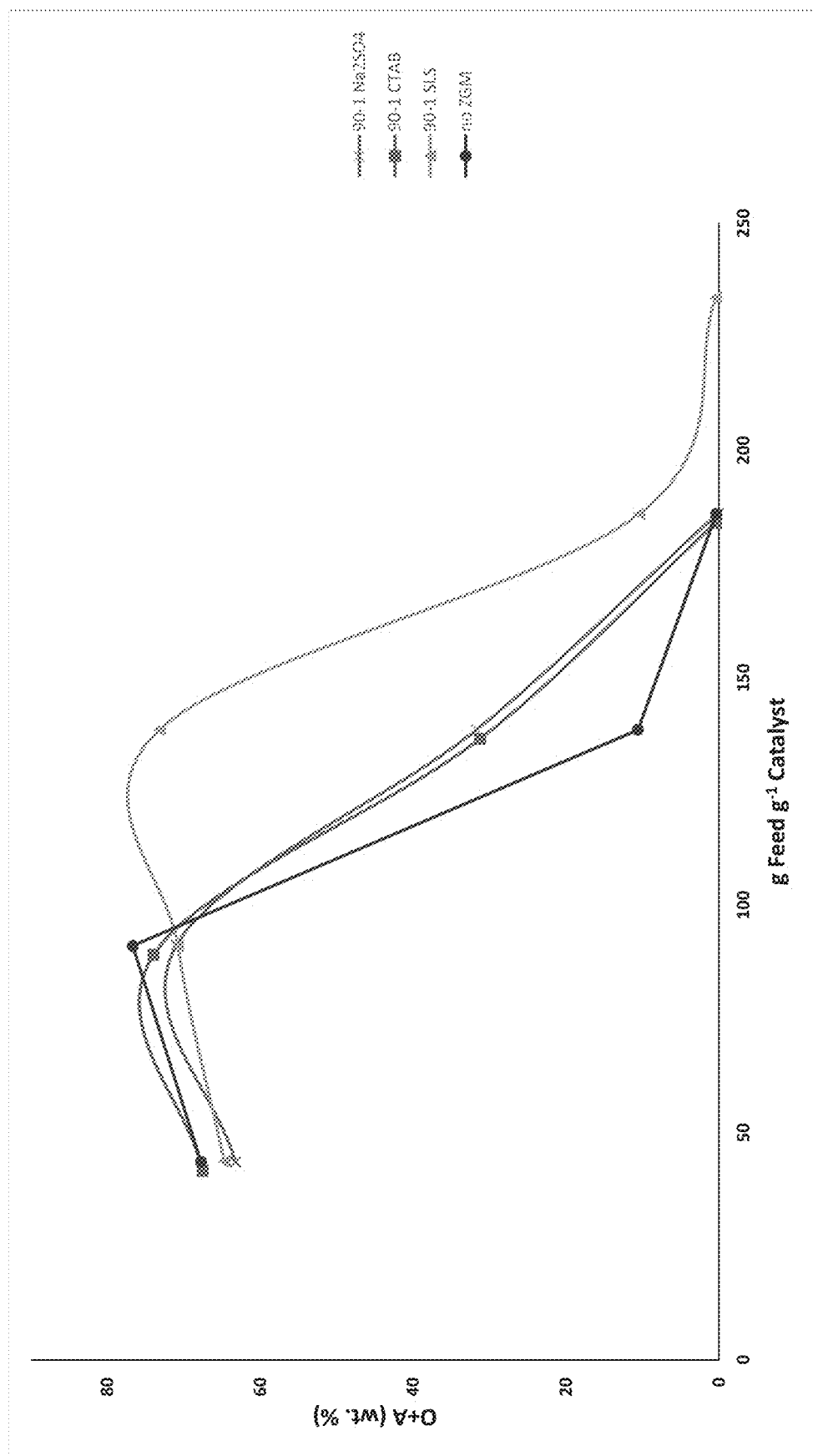
FIG. 7 shows combined olefin plus aromatics yield versus the amount of methanol exposure for ZSM-48 catalysts synthesized with various zeolite growth modifiers.
Figure 8:
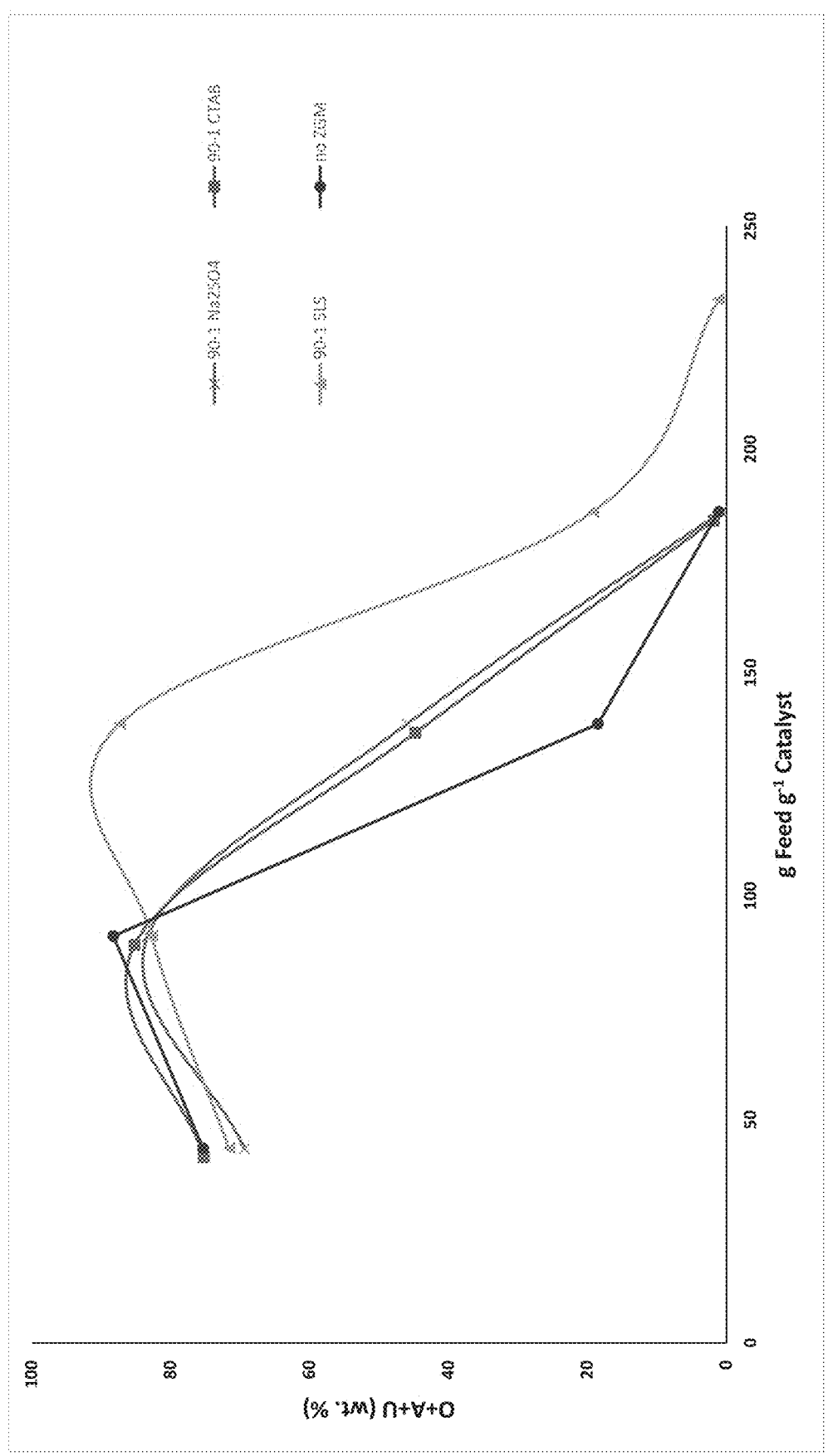
FIG. 8 shows combined olefin, aromatics, and unknowns yield versus the amount of methanol exposure for ZSM-48 catalysts synthesized with various zeolite growth modifiers.

FIGS. 5 to 8 show results from the methanol conversion tests. FIG. 5 shows olefin yield relative to the amount of methanol exposed to the catalyst (g MeOH/g catalyst). FIG. 6 shows paraffin yield relative to the methanol exposure. FIG. 7 shows combined olefin and aromatics yield relative to the methanol exposure. Similar to FIG. 4, FIG. 8 shows combined olefin, aromatics, and unknowns yield relative to the methanol exposure.

As shown in FIG. 5, addition of SLS as a modifier has a substantial impact on catalyst lifetime, with the yield of olefins staying above zero until well past 200 g/MeOH/g catalyst. It is noted that the SLS growth modifier resulted in the smallest median crystal length (41 nm) for the growth modifiers tested for methanol conversion. Addition of sodium sulfate or CTAB had a more modest effect, with similar total lifetime to the reference catalyst, but a higher production of olefins toward the end of the catalyst lifetime at around 150 g MeOH/g catalyst.

The paraffin yields in FIG. 6 are similar to the results shown in FIG. 5, with the exception that the addition of sodium sulfate resulted in some additional initial yield of paraffins. However, the lifetime trends for each growth modifier in FIG. 6 are similar to those in FIG. 5. FIG. 7, which shows combined olefin and aromatic yields, and FIG. 8, which shows combined olefin, aromatic, and unknown yields, also show trends similar to those in FIG. 5. Thus, FIGS. 7 and 8 show an unexpected improvement in catalyst lifetime for the small crystal length ZSM-48 catalyst (synthesized using SLS).

The invention claimed is:

1. A process of preparing crystals of a molecular sieve having a framework code selected from the group consisting of MEI, TON, MRE, MWW, MPS, MOR, FAU, EMT, and MSE, the process comprising the steps of:
   a. combining at least a source of a tetravalent element X, a morphology modifier L, and water to form a synthesis mixture wherein the morphology modifier L is combined before nucleation or crystallization starts;
   b. heating said synthesis mixture under crystallization conditions for a time of about 1 hour to 100 days to form the crystals of the molecular sieve; and
   c. recovering said crystals of the molecular sieve from the synthesis mixture,
   wherein X=Si, and the morphology modifier L is a sugar, a nonionic surfactant, or an anionic surfactant, and the morphology modifier L is present in the synthesis mixture in a concentration in the range of from 0.01 wt % to 10 wt %, and if a structure directing agent Q is present, L is different from and is present in addition to the structure directing agent Q.

2. A process as claimed in claim 1 in which in step a) one or more further components selected from the group consisting of a source of hydroxide ions, a structure directing agent Q, a source of a trivalent element Y, a source of a pentavalent element Z, a source of halide ions W$^-$, and a source of alkali metal ions M$^+$ and/or a source of alkali earth metal cations M$^{2+}$, are also combined into the synthesis mixture.

3. A process as claimed in claim 2 in which the ratio Q:(XO$_2$+Y$_2$O$_3$+Z$_2$O$_5$) is in the range of from 0.01 to 1.0.

4. A process as claimed in claim 1 in which the molar ratio L:X in the synthesis mixture is in the range of from 0.001 to 0.03.

5. A process as claimed in claim 1 in which a source of a trivalent element Y is present in the synthesis mixture and Y is Al, and the ratio of XO$_2$:Y$_2$O$_3$ is in the range of from 5 to 500.

6. A process as claimed in claim 1 in which the synthesis mixture is substantially free of water-insoluble liquid components.

7. A process as claimed in claim 1 which includes the step of calcining the crystals recovered in step c) to give the calcined form of the molecular sieve.

8. A process as claimed in claim 1 in which the molecular sieve is a zeolite selected from the group consisting of ZSM-18, ZSM-22, ZSM-48, MCM-49, ZSM-57, mordenite, cubic faujasite, hexagonal faujasite and MCM-68.

* * * * *